US012741955B2

(12) United States Patent
Ji

(10) Patent No.: US 12,741,955 B2

(45) Date of Patent: Sep. 22, 2026

(54) TARGETING PLECKSTRIN-2 FOR TREATING CANCER AND OTHER DISEASES AND DISORDERS

(71) Applicant: Northwestern University, Evanston, IL (US)

(72) Inventor: Peng Ji, Evanston, IL (US)

(73) Assignee: Northwestern University, Evanston, IL (US)

( * ) Notice: Subject to any disclaimer, the term of this patent is extended or adjusted under 35 U.S.C. 154(b) by 454 days.

(21) Appl. No.: 18/260,373

(22) PCT Filed: Jan. 6, 2022

(86) PCT No.: PCT/US2022/070063

§ 371 (c)(1),
(2) Date: Jul. 5, 2023

(87) PCT Pub. No.: WO2022/150827

PCT Pub. Date: Jul. 14, 2022

(65) Prior Publication Data

US 2024/0083874 A1 Mar. 14, 2024

Related U.S. Application Data

(60) Provisional application No. 63/134,539, filed on Jan. 6, 2021.

(51) Int. Cl.

| | |
|---|---|
| ***C07D 401/14*** | (2006.01) |
| ***A61K 47/54*** | (2017.01) |
| ***A61P 35/02*** | (2006.01) |

(52) U.S. Cl.

CPC ............ *C07D 401/14* (2013.01); *A61K 47/54* (2017.08); *A61P 35/02* (2018.01)

(58) Field of Classification Search

CPC ......... C07D 401/14; A61P 35/00; A61P 35/02

See application file for complete search history.

(56) References Cited

U.S. PATENT DOCUMENTS

2005/0153966 A1 7/2005 Gangloff et al.

FOREIGN PATENT DOCUMENTS

WO 2020092950 A1 5/2020

OTHER PUBLICATIONS

Han et al., "Abstract 1287: Targeting pleckstrin-2 for the JAK2-STAT andPI3K-Akt pathways in cancer therapy", 2019, Cancer Research, 79, Abstract 1287 (Year: 2019).*

Abrams CS, Zhang J, Downes CP, Tang X, Zhao W, Rittenhouse SE. Phosphopleckstrin inhibits gbetagamma-activable platelet phosphatidylinositol-4,5-bisphosphate 3-kinase. J Biol Chem. 1996;271(41):25192-7. Epub Oct. 11, 1996. PubMed PMID: 8810277.

Araki M, Yang Y, Masubuchi N, Hironaka Y, Takei H, Morishita S, Mizukami Y, Kan S, Shirane S, Edahiro Y, Sunami Y, Ohsaka A, Komatsu N. Activation of the thrombopoietin receptor by mutant calreticulin in CALRmutant myeloproliferative neoplasms. Blood. 2016;127(10):1307-16. Epub Jan. 29, 2016. doi: 10.1182/blood-2015-09-671172. PubMed PMID: 26817954.

Bach TL, Kerr WT, Wang Y, Bauman EM, Kine P, Whiteman EL, Morgan RS, Williamson EK, Ostap EM, Burkhardt JK, Koretzky GA, Birnbaum MJ, Abrams CS. PI3K regulates pleckstrin-2 in T-cell cytoskeletal reorganization. Blood. 2007;109(3):1147-55. Epub Sep. 30, 2006. doi: 10.1182/blood-2006-02-001339. PubMed PMID: 17008542; PMCID: PMC1785144.

Bartalucci N, Guglielmelli P, Vannucchi AM. Rationale for targeting the PI3K/Akt/mTOR pathway in myeloproliferative neoplasms. Clin Lymphoma Myeloma Leuk. 2013;13 Suppl 2:S307-9. Epub Dec. 7, 2013. doi: 10.1016/j.clml.2013.07.011. PubMed PMID: 24290217.

Baxter EJ, Scott LM, Campbell PJ, East C, Fourouclas N, Swanton S, Vassiliou GS, Bench AJ, Boyd EM, Curtin N, Scott MA, Erber WN, Green AR, Cancer Genome P. Acquired mutation of the tyrosine kinase JAK2 in human myeloproliferative disorders. Lancet. 2005;365(9464):1054-61. Epub Mar. 23, 2005. doi: 10.1016/S0140-6736(05) 71142-9. PubMed PMID: 15781101.

Bondeson DP, Smith BE, Burslem GM, Buhimschi AD, Hines J, Jaime-Figueroa S, Wang J, Hamman BD, Ishchenko A, Crews CM. Lessons in PROTAC Design from Selective Degradation with a Promiscuous Warhead. Cell Chem Biol. 2018;25(1):78-87 e5. Epub Nov. 14, 2017. doi: 10.1016/j.chembiol.2017.09.010. PubMed PMID: 29129718; PMCID: PMC5777153.

Butler KV, Ma A, Yu W, Li F, Tempel W, Babault N, Pittella-Silva F, Shao J, Wang J, Luo M, Vedadi M, Brown PJ, Arrowsmith CH, Jin J. Structure-Based Design of a Covalent Inhibitor of the SET Domain-Containing Protein 8 (SETD8) Lysine Methyltransferase. J Med Chem. 2016;59(21):9881-9. Epub Nov. 3, 2016. doi: 10.1021/acs.jmedchem.6b01244. PubMed PMID: 27804297; PMCID: PMC5148670.

Caroni P. New EMBO members' review: actin cytoskeleton regulation through modulation of PI(4,5)P(2) rafts. EMBO J. 2001;20(16):4332-6. Epub Aug. 14, 2001. doi: 10.1093/emboj/20.16.4332. PubMed PMID: 11500359; PMCID: PMC125564.

(Continued)

*Primary Examiner* — Brenda L Coleman
*Assistant Examiner* — Madeline E Braun
(74) *Attorney, Agent, or Firm* — Quarles & Brady LLP

(57) ABSTRACT

Disclosed are small molecule inhibitors of Plek2 biological activity. The compositions and method may be utilized for treating cell proliferative diseases and disorders and other diseases and disorders, such as diseases and disorders that are characterized by Plek2 expression and/or by activation of the phosphatidylinositide 3-kinase (PI3K)/Akt pathway. Cell proliferative diseases and disorders that may be treated using the disclosed compositions and methods may include, but are not limited to, myeloproliferative neoplasms (MPNs) such as Philadelphia (Ph)-negative MPNs, and cancers such as acute myeloid leukemia (AML) and cancers characterized by solid tumors.

9 Claims, 10 Drawing Sheets

Specification includes a Sequence Listing.

(56) References Cited

OTHER PUBLICATIONS

Cervantes F, Vannucchi AM, Kiladjian JJ, Al-Ali HK, Sirulnik A, Stalbovskaya V, McQuitty M, Hunter DS, Levy RS, Passamonti F, Barbui T, Barosi G, Harrison CN, Knoops L, Gisslinger H, investigators C-I. Three-year efficacy, safety, and survival findings from COMFORT-II, a phase 3 study comparing ruxolitinib with best available therapy for myelofibrosis. Blood. 2013;122(25):4047-53. Epub Nov. 1, 2013. doi: 10.1182/blood-2013-02-485888. PubMed PMID: 24174625.
Chen VB, Arendall WB, 3rd, Headd JJ, Keedy DA, Immormino RM, Kapral GJ, Murray LW, Richardson JS, Richardson DC. MolProbity: all-atom structure validation for macromolecular crystallography. Acta Crystallogr D Biol Crystallogr. 2010;66(Pt 1): 12-21. Epub Jan. 9, 2010. doi: 10.1107/S0907444909042073. PubMed PMID: 20057044; PMCID: PMC2803126.
Choong ML, Pecquet C, Pendharkar V, Diaconu CC, Yong JW, Tai SJ, Wang SF, Defour JP, Sangthongpitag K, Villeval JL, Vainchenker W, Constantinescu SN, Lee MA. Combination treatment for myeloproliferative neoplasms using JAK and pan-class I PI3K inhibitors. J Cell Mol Med. 2013;17(11):1397-409. Epub Nov. 21, 2013. doi: 10.1111/jcmm.12156. PubMed PMID: 24251790; PMCID: PMC4117552.
Deschaies, "Prime Time for PROTACS," Nature Chem. Biol., 11, 634-635 (2015).
Elf S, Abdelfattah NS, Chen E, Perales-Paton J, Rosen EA, Ko A, Peisker F, Florescu N, Giannini S, Wolach O, Morgan EA, Tothova Z, Losman JA, Schneider RK, Al-Shahrour F, Mullally A. Mutant Calreticulin Requires Both Its Mutant C-terminus and the Thrombopoietin Receptor for Oncogenic Transformation. Cancer Discov. 2016;6(4):368-81. Epub Mar. 10, 2016. doi: 10.1158/2159-8290.CD-15-1434. PubMed PMID: 26951227; PMCID: PMC4851866.
Fischer B, Luthy K, Paesmans J, De Koninck C, Maes I, Swerts J, Kuenen S, Uytterhoeven V, Verstreken P, Versees W. Skywalker-TBC1D24 has a lipid-binding pocket mutated in epilepsy and required for synaptic function. Nat Struct Mol Biol. 2016;23(11):965-73. Epub Nov. 1, 2016. doi: 10.1038/nsmb.3297. PubMed PMID: 27669036.
Fiskus W, Verstovsek S, Manshouri T, Smith JE, Peth K, Abhyankar S, McGuirk J, Bhalla KN. Dual PI3K/AKT/mTOR inhibitor BEZ235 synergistically enhances the activity of JAK2 inhibitor against cultured and primary human myeloproliferative neoplasm cells. Mol Cancer Ther. 2013; 12(5):577-88. Epub Mar. 1, 2013. doi: 10.1158/1535-7163. MCT-12-0862. PubMed PMID: 23445613.
Gu et al., "PROTACs: An Emerging Targeting Technique for Protein Degradation in Drug Discovery," BioEssays, 2018, 40 17000247, 1-11.
Hamaguchi N, Ihara S, Ohdaira T, Nagano H, Iwamatsu A, Tachikawa H, Fukui Y. Pleckstrin-2 selectively interacts with phosphatidylinositol 3-kinase lipid products and regulates actin organization and cell spreading. Biochem Biophys Res Commun. 2007;361(2):270-5. Epub Jul. 31, 2007. doi: 10.1016/j.bbrc.2007.06.132. PubMed PMID: 17658464.
Harrison C, Kiladjian JJ, Al-Ali HK, Gisslinger H, Waltzman R, Stalbovskaya V, McQuitty M, Hunter DS, Levy R, Knoops L, Cervantes F, Vannucchi AM, Barbui T, Barosi G. Jak inhibition with ruxolitinib versus best available therapy for myelofibrosis. N Engl J Med. 2012;366(9):787-98. Epub Mar. 2, 2012. doi: 10.1056/NEJMoa1110556. PubMed PMID: 22375970.
Hresko RC, Murata H, Mueckler M. Phosphoinositide-dependent kinase-2 is a distinct protein kinase enriched in a novel cytoskeletal fraction associated with adipocyte plasma membranes. J Biol Chem. 2003;278(24):21615-22. Epub Apr. 19, 2003. doi: 10.1074/jbc. M302937200. PubMed PMID: 12682057.
Hu MH, Bauman EM, Roll RL, Yeilding N, Abrams CS. Pleckstrin 2, a widely expressed paralog of pleckstrin involved in actin rearrangement. J Biol Chem. 1999;274(31):21515-8. Epub Jul. 27, 1999. PubMed PMID: 10419454.
Isakoff SJ, Cardozo T, Andreev J, Li Z, Ferguson KM, Abagyan R, Lemmon MA, Aronheim A, Skolnik EY. Identification and analysis of PH domain-containing targets of phosphatidylinositol 3-kinase using a novel in vivo assay in yeast. EMBO J. 1998;17(18):5374-87. Epub Sep. 16, 1998. doi: 10.1093/emboj/17.18.5374. PubMed PMID: 9736615; PMCID: PMC1170863.
James C, Ugo V, Le Couedic JP, Staerk J, Delhommeau F, Lacout C, Garcon L, Raslova H, Berger R, Bennaceur- Griscelli A, Villeval JL, Constantinescu SN, Casadevall N, Vainchenker W. A unique clonal JAK2 mutation leading to constitutive signalling causes polycythaemia vera. Nature. 2005;434(7037):1144-8. Epub Mar. 29, 2005. doi: 10.1038/nature03546. PubMed PMID: 15793561.
Ji P, Jayapal SR, Lodish HF. Enucleation of cultured mouse fetal erythroblasts requires Rac GTPases and mDia2. Nat Cell Biol. 2008;10(3):314-21. Epub Feb. 12, 2008. doi: 10.1038/ncb1693. PubMed PMID: 18264091.
Kleppe M, Kwak M, Koppikar P, Riester M, Keller M, Bastian L, Hricik T, Bhagwat N, McKenney AS, Papalexi E, Abdel-Wahab O, Rampal R, Marubayashi S, Chen JJ, Romanet V, Fridman JS, Bromberg J, Teruya-Feldstein J, Murakami M, Radimerski T, Michor F, Fan R, Levine RL. JAK-STAT pathway activation in malignant and nonmalignant cells contributes to MPN pathogenesis and therapeutic response. Cancer Discov. 2015;5(3):316-31. Epub Jan. 13, 2015. doi: 10.1158/2159-8290.CD-14-0736. PubMed PMID: 25572172; PMCID: PMC4355105.
Koppikar P, Bhagwat N, Kilpivaara O, Manshouri T, Adli M, Hricik T, Liu F, Saunders LM, Mullally A, Abdel-Wahab O, Leung L, Weinstein A, Marubayashi S, Goel A, Gonen M, Estrov Z, Ebert BL, Chiosis G, Nimer SD, Bernstein BE, Verstovsek S, Levine RL. Heterodimeric JAK-STAT activation as a mechanism of persistence to JAK2 inhibitor therapy. Nature. 2012;489(7414):155-9. Epub Jul. 24, 2012. doi: 10.1038/nature11303. PubMed PMID: 22820254; PMCID: PMC3991463.
Kralovics R, Passamonti F, Buser AS, Teo SS, Tiedt R, Passweg JR, Tichelli A, Cazzola M, Skoda RC. A gain-of-function mutation of JAK2 in myeloproliferative disorders. N Engl J Med. 2005;352(17):1779-90. Epub Apr. 29, 2005. doi: 10.1056/NEJMoa051113. PubMed PMID: 15858187.
Kralovics R, Teo SS, Buser AS, Brutsche M, Tiedt R, Tichelli A, Passamonti F, Pietra D, Cazzola M, Skoda RC. Altered gene expression in myeloproliferative disorders correlates with activation of signaling by the V617F mutation of Jak2. Blood. 2005; 106(10):3374-6. Epub Aug. 6, 2005. doi: 10.1182/blood-2005-05-1889. PubMed PMID: 16081684.
Kurokawa T, Takasuga S, Sakata S, Yamaguchi S, Horie S, Homma KJ, Sasaki T, Okamura Y. 3' Phosphatase activity toward phosphatidylinositol 3,4-bisphosphate [PI(3,4)P2] by voltage-sensing phosphatase (VSP). Proc Natl Acad Sci U S A. 2012; 109(25):10089-94. Epub May 31, 2012. doi: 10.1073/pnas. 1203799109. PubMed PMID: 22645351; PMCID: PMC3382541.
Laux T, Fukami K, Thelen M, Golub T, Frey D, Caroni P. GAP43, Marcks, and CAP23 modulate PI(4,5)P(2) at plasmalemmal rafts, and regulate cell cortex actin dynamics through a common mechanism. J Cell Biol. 2000;149 (7):1455-72. Epub Jun. 28, 2000. PubMed PMID: 10871285; PMCID: PMC2175130.
Lemmon MA, Ferguson KM, Abrams CS. Pleckstrin homology domains and the cytoskeleton. FEBS Lett. 2002;513 (1):71-6. Epub Mar. 26, 2002. PubMed PMID: 11911883.
Lemmon MA, Ferguson KM, O'Brien R, Sigler PB, Schlessinger J. Specific and high-affinity binding of inositol phosphates to an isolated pleckstrin homology domain. Proc Natl Acad Sci U S A. 1995;92(23):10472-6. Epub Nov. 7, 1995. PubMed PMID: 7479822; PMCID: PMC40633.
Lemmon MA. Membrane recognition by phospholipid-binding domains. Nat Rev Mol Cell Biol. 2008;9(2):99-111. Epub Jan. 25, 2008. doi: 10.1038/nrm2328. PubMed PMID: 18216767.
Levine RL, Wadleigh M, Cools J, Ebert BL, Wernig G, Huntly BJ, Boggon TJ, Wlodarska I, Clark JJ, Moore S, Adelsperger J, Koo S, Lee JC, Gabriel S, Mercher T, D'Andrea A, Frohling S, Dohner K, Marynen P, Vandenberghe P, Mesa RA, Tefferi A, Griffin JD, Eck MJ, Sellers WR, Meyerson M, Golub TR, Lee SJ, Gilliland DG. Activating mutation in the tyrosine kinase JAK2 in polycythemia vera, essential thrombocythemia, and myeloid metaplasia with

(56) References Cited

OTHER PUBLICATIONS myelofibrosis. Cancer Cell. 2005;7(4):387-97. Epub Apr. 20, 2005. doi: 10.1016/j.ccr.2005.03.023. PubMed PMID: 15387627.
Liepina I, Czaplewski C, Janmey P, Liwo A. Molecular dynamics study of a gelsolin-derived peptide binding to a lipid bilayer containing phosphatidylinositol 4,5-bisphosphate. Biopolymers. 2003;71(1):49-70. Epub Apr. 25, 2003. doi: 10.1002/bip.10375. PubMed PMID: 12712500.
Lonsdale R, Ward RA. Structure-based design of targeted covalent inhibitors. Chemical Society reviews. 2018;47 (11):3816-30. Epub Apr. 6, 2018. doi: 10.1039/c7cs00220c. PubMed PMID: 29620097.
Ma AD, Abrams CS. Pleckstrin induces cytoskeletal reorganization via a Rac-dependent pathway. J Biol Chem. 1999;274(40):28730-5. Epub Sep. 25, 1999. PubMed PMID: 10497244.
McLaughlin S, Murray D. Plasma membrane phosphoinositide organization by protein electrostatics. Nature. 2005;438 (7068):605-11. Epub Dec. 2, 2005. doi: 10.1038/nature04398. PubMed PMID: 16319880.
McLoman et al., "JAK2 V617F: A Single Mutation in the Myeloproliferative Group of Disorders," Ulster Med. J., May 2006; 75(2):112-119.
Mishra RK, Wei C, Hresko RC, Bajpai R, Heitmeier M, Matulis SM, Nooka AK, Rosen ST, Hruz PW, Schiltz GE, Shanmugam M. In Silico Modeling-based Identification of Glucose Transporter 4 (GLUT4)-selective Inhibitors for Cancer Therapy. J Biol Chem. 2015;290(23):14441-53. Epub Apr. 8, 2015. doi: 10.1074/jbc.M114.628826. PubMed PMID: 25847249; PMCID: PMC4505511.
Neklesa TK, Winkler JD, Crews CM. Targeted protein degradation by PROTACs. Pharmacology & therapeutics. 2017;174:138-44. Epub Feb. 23, 2017. doi: 10.1016/j.pharmthera.2017.02.027. PubMed PMID: 28223226.
Passamonti F, Maffioli M. The role of JAK2 inhibitors in MPNs 7 years after approval. Blood. 2018;131(22):2426-35. Epub Apr. 14, 2018. doi: 10.1182/blood-2018-01-791491. PubMed PMID: 29650801.
Pikman Y, Lee BH, Mercher T, McDowell E, Ebert BL, Gozo M, Cuker A, Wernig G, Moore S, Galinsky I, DeAngelo DJ, Clark JJ, Lee SJ, Golub TR, Wadleigh M, Gilliland DG, Levine RL. MPLW515L is a novel somatic activating mutation in myelofibrosis with myeloid metaplasia. PLoS Med. 2006;3(7):e270. Epub Jul. 13, 2006. doi: 10.1371/journal.pmed.0030270. PubMed PMID: 16834459; PMCID: PMC1502153.
Porpaczy E, Tripolt S, Hoelbl-Kovacic A, Gisslinger B, Bago-Horvath Z, Casanova-Hevia E, Clappier E, Decker T, Fajmann S, Fux DA, Greiner G, Gueltekin S, Heller G, Herkner H, Hoermann G, Kiladjian JJ, Kolbe T, Kornauth C, Krauth MT, Kralovics R, Muellauer L, Mueller M, Prchal-Murphy M, Putz EM, Raffoux E, Schiefer AI, Schmetterer K, Schneckenleithner C, Simonitsch-Klupp I, Skrabs C, Sperr WR, Staber PB, Strobl B, Valent P, Jaeger U, Gisslinger H, Sexl V. Aggressive B-cell lymphomas in patients with myelofibrosis receiving JAK1/2 inhibitor therapy. Blood. 2018.
Rampal R, Al-Shahrour F, Abdel-Wahab O, Patel JP, Brunel JP, Mermel CH, Bass AJ, Pretz J, Ahn J, Hricik T, Kilpivaara O, Wadleigh M, Busque L, Gilliland DG, Golub TR, Ebert BL, Levine RL. Integrated genomic analysis illustrates the central role of JAK-STAT pathway activation in myeloproliferative neoplasm pathogenesis. Blood. 2014;123(22):e123-33. Epub Apr. 18, 2014. doi: 10.1182/blood-2014-02-554634. PubMed PMID: 24740812; PMCID: PMC4041169.
Schulz-Gasch T, Stahl M. Binding site characteristics in structure-based virtual screening: evaluation of current docking tools. J Mol Model. 2003;9(1):47-57. Epub Mar. 15, 2003. doi: 10.1007/s00894-002-0112-y. PubMed PMID: 12638011.
Sheetz MP. Cell control by membrane-cytoskeleton adhesion. Nat Rev Mol Cell Biol. 2001;2(5):392-6. Epub May 2, 2001. doi: 10.1038/35073095. PubMed PMID: 11331914.
Sherman W, Day T, Jacobson MP, Friesner RA, Farid R. Novel procedure for modeling ligand/receptor induced fit effects. J Med Chem. 2006;49(2):534-53. Epub Jan. 20, 2006. doi: 10.1021/jm050540c. PubMed PMID: 16420040.
Sonbol MB, Firwana B, Zarzour A, Morad M, Rana V, Tiu RV. Comprehensive review of JAK inhibitors in myeloproliferative neoplasms. Ther Adv Hematol. 2013;4(1):15-35. Epub Apr. 24, 2013. doi: 10.1177/2040620712461047. PubMed PMID: 23610611; PMCID: PMC3629759.
Tefferi A, Pardanani A. Myeloproliferative Neoplasms: A Contemporary Review. JAMA Oncol. 2015;1(1):97-105. Epub Jul. 17, 2015. doi: 10.1001/jamaoncol.2015.89. PubMed PMID: 26182311.
Vannucchi AM, Harrison CN. Emerging treatments for classical myeloproliferative neoplasms. Blood. 2017; 129 (6):693-703. Epub Dec. 29, 2016. doi: 10.1182/blood-2016-10-695965. PubMed PMID: 28028027.
Wang Y, Chen X, Lian L, Tang T, Stalker TJ, Sasaki T, Kanaho Y, Brass LF, Choi JK, Hartwig JH, Abrams CS. Loss of PIP5KIbeta demonstrates that PIP5KI isoform-specific PIP2 synthesis is required for IP3 formation. Proc Natl Acad Sci USA. 2008;105(37):14064-9. Epub Sep. 6, 2008. doi: 10.1073/pnas.0804139105. PubMed PMID: 18772378; PMCID: PMC2544579.
Wang Y, Litvinov RI, Chen X, Bach TL, Lian L, Petrich BG, Monkley SJ, Kanaho Y, Critchley DR, Sasaki T, Birnbaum MJ, Weisel JW, Hartwig J, Abrams CS. Loss of PIP5KIgamma, unlike other PIP5KI isoforms, impairs the integrity of the membrane cytoskeleton in murine megakaryocytes. J Clin Invest. 2008; 118(2):812-9. Epub Jan. 12, 2008. doi: 10.1172/JCI34239. PubMed PMID: 18188447; PMCID: PMC2176194.
Wen QJ, Yang Q, Goldenson B, Malinge S, Lasho T, Schneider RK, Breyfogle LJ, Schultz R, Gilles L, Koppikar P, Abdel-Wahab O, Pardanani A, Stein B, Gurbuxani S, Mullally A, Levine RL, Tefferi A, Crispino JD. Targeting megakaryocytic-induced fibrosis in myeloproliferative neoplasms by AURKA inhibition. Nat Med. 2015;21(12):1473-80. Epub Nov. 17, 2015. doi: 10.1038/nm.3995. PubMed PMID: 26569382; PMCID: PMC4674320.
Yilmaz OH, Valdez R, Theisen BK, Guo W, Ferguson DO, Wu H, Morrison SJ. Pten dependence distinguishes haematopoietic stem cells from leukaemia-initiating cells. Nature. 2006;441(7092):475-82. Epub Apr. 7, 2006. doi: 10.1038/nature04703. PubMed PMID: 16598206.
Yu JW, Mendrola JM, Audhya A, Singh S, Keleti D, DeWald DB, Murray D, Emr SD, Lemmon MA. Genome-wide analysis of membrane targeting by *S. cerevisiae* pleckstrin homology domains. Mol Cell. 2004;13(5):677-88. Epub Mar. 17, 2004. PubMed PMID: 15023338.
Zhao B, Mei Y, Cao L, Zhang J, Sumagin R, Yang J, Gao J, Schipma MJ, Wang Y, Thorsheim C, Zhao L, Stalker T, Stein B, Wen QJ, Crispino JD, Abrams CS, Ji P. Loss of pleckstrin-2 reverts lethality and vascular occlusions in JAK2V617F-positive myeloproliferative neoplasms. J Clin Invest. 2018;128(1):125-40. Epub Dec. 5, 2017. doi: 10.1172/JCI94518. PubMed PMID: 29202466.
Zhou LP, Yang LH, Tilton S, Wang JL. Development of a high throughput equilibrium solubility assay using miniaturized shake-flask method in early drug discovery. J Pharm Sci-Us. 2007; 96(11):3052-71. doi: Doi 10.1002/Jps.20913. PubMed PMID: WOS:000250618700018.
PUBCHEM, SID 249092339, Modify Date: Jan. 26, 2017 (retrieved on Mar. 2, 2022]. Retrieved from the Internet: <URL: https://pubchem.ncbi.nlm.nih.gov/substance/249092339> entire document.
International Search Report, corresponding to PCT/US2022/070063, dated Jun. 2, 2022.

* cited by examiner

Structure of NUP-52A

The optimized lead compound has similar efficacies as FDA-approved JAK2 inhibitor in blocking cell proliferation

E

F

TARGETING PLECKSTRIN-2 FOR TREATING CANCER AND OTHER DISEASES AND DISORDERS

CROSS-REFERENCE TO RELATED PATENT APPLICATIONS

This application represents the National Stage entry of PCT/US2022/070063 filed on Jan. 6, 2022, which claims the benefit of priority under 35 U.S.C. § 119(e) to U.S. Provisional Application No. 63/134,539, filed on Jan. 6, 2021. The contents of each is incorporated herein by reference in their entireties.

REFERENCE TO A SEQUENCE LISTING SUBMITTED VIA EFS-WEB

The content of the ASCII text file of the sequence listing names "702581_01895_ST25.txt" which is 3.24 kb in size was created on January 6, 2021 and electronically submitted via EFS-Web herewith the application is incorporated herein by reference in its entirety.

BACKGROUND

The field of the invention relates to methods for treating cancers and other diseases and disorders associated with Pleckstrin-2 (Plek2). In particular, the field of the invention relates to methods for treating cancer and other diseases and disorders associated with Plek2 by targeting Plek2 with small molecule inhibitors.

Myeloproliferative neoplasms (MPNs) are a group of bone marrow diseases with excessive production of myeloid cells, increased risk of arterial or venous thrombosis, and a propensity to transform into acute myeloid leukemia (AML). Current therapies for MPNs are not curative and have significant drug resistance and side effects, which necessitate new therapeutic strategies. For example, the Janus kinase 2 (JAK2) V617F mutation, which results in JAK2 dysregulation, is found in the majority of Philadelphia chromosome (Ph)-negative myeloproliferative neoplasms (MPNs). (See, e.g., McLoman et al., "JAK2 V617F: A Single Mutation in the Myeloproliferative Group of Disorders," Ulster Med. J., 2006 May; 75(2):112-119, the content of which is incorporated by reference in its entirety). As such, therapy using JAK2 inhibitors that are targeted at JAK2 dysregulation have been one of the mainstays for treating Ph-negative MPNs. However, JAK2 inhibitors face many challenges including drug resistance and severe side effects.

A published work reveals a novel target, named Pleckstrin-2 (Plek2), which is highly expressed in MPNs. (See Zhao et al., "Loss of pleckstrin-2 reverts lethality and vascular occlusions in JAK2V617F-positive myeloproliferative neoplasms, J. Clin. Invest., Nov. 20, 2017, the content of which is incorporated herein by reference in its entirety). Here, through medicinal chemistry, novel small molecule Plek2 inhibitors have been identified. The identified Plek2 inhibitors show potent inhibitory effects on several in vitro and in vivo models of MPNs. The identified Plek2 inhibitors are expected to have significant advantages over the current drugs for MPN treatment in that they will decrease the incidence of blood clot formation, which is a major risk of mortality and mobility, and have significant less side effects.

SUMMARY

Disclosed herein are compounds, compositions, and methods for treating diseases and disorders associated with Pleckstrin-2 (Plek2) activity based on the discovery that Plek2 can be targeted with small molecule inhibitors. The compositions and methods disclosed herein typically include or utilize the disclosed compounds as therapeutic agents which inhibit the biological activity or expression of Pleckstrin-2 (Plek2) and collectively may be referred to as "Plek2 inhibitors."

Particularly disclosed are small molecule inhibitors of Plek2 biological activity. The compositions and methods may be utilized for treating cell proliferative diseases and disorders and other diseases and disorders that are characterized by elevated levels of Plek2 expression and/or by activation of the phosphatidylinositide 3-kinase (PI3K)/Akt pathway. Diseases and disorders that may be treated using the disclosed compositions and methods may include, but are not limited to, myeloproliferative neoplasms (MPNs) such as Philadelphia (Ph)-negative MPNs, and diseases and disorders such as acute myeloid leukemia (AML) and cancers characterized by solid tumors, such as colorectal carcinoma, pancreatic cancer, lung cancer, renal carcinoma, and breast cancer.

DETAILED DESCRIPTION

Figure 1:
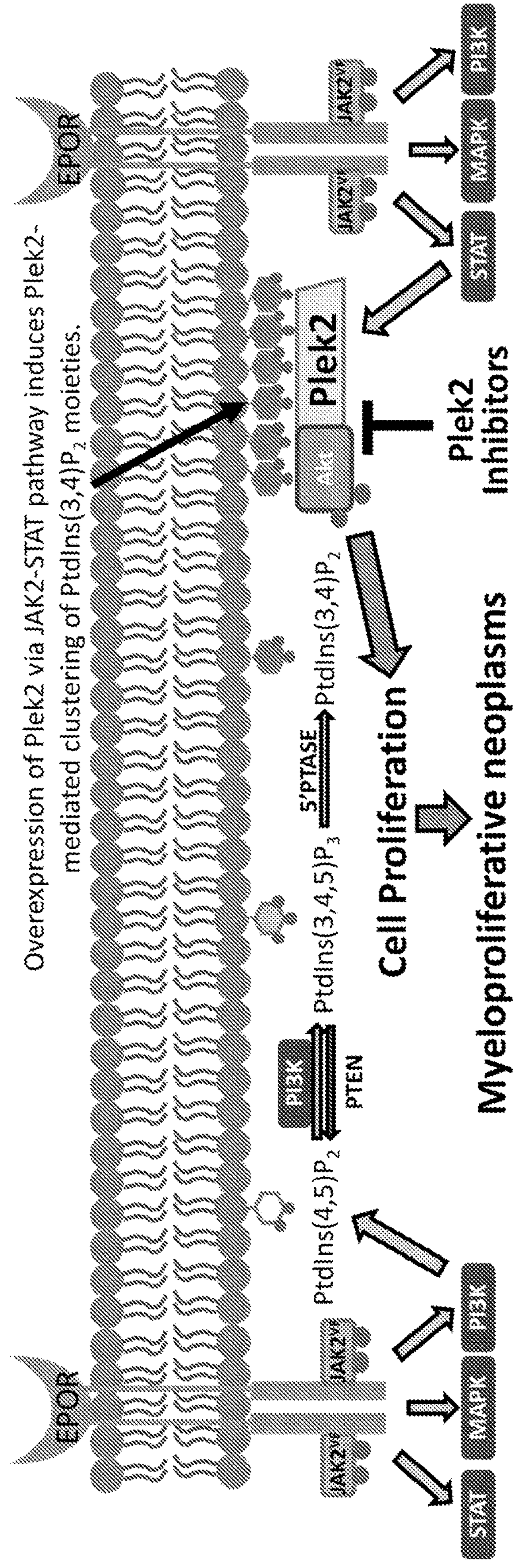
FIG. 1. Schematic view of the proposed mechanism of Plek2 function and drug target route. JAK2VF represents JAK2V617F mutant.

The present invention is described herein using several definitions, as set forth below and throughout the application.

Definitions

Unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more therapeutic agents that inhibit the biological activity or expression of Pleckstrin-2 (Plek2). A "subject in need of treatment" may include a subject having a disease or disorder associated with expression or overexpression of Plek2, for example overexpression of an mRNA encoding the Plek2 protein. A "subject in need of treatment" may include a subject having a disease or disorder associated with activation of the phosphatidylinositide 3-kinase (PI3K)/Akt pathway.

The pleckstrin-2 (Plek2) protein is known in the art. The 353 amino acid sequence for the human Plek2 protein is deposited at GenBank as NCBI Reference Sequence: NP_057529.1. (See also SEQ ID NO:1).

```
                                         SEQ ID NO: 1
  1  medgvlkegf lvkrghivhn wkarwfilrq ntlvyykleg
     grrvtppkgr illdgctitc
 61  pcleyenrpl liklktqtst eyfleacsre erdawafeit
     gaihagqpgk vqqlhslrns
121  fklpphislh rivdkmhdsn tgirsspnme qgstykktfl
     gsslvdwlis nsftasrlea
181  vtlasmlmee nflrpvgvrs mgairsgdla eqflddstal
     ytfaesykkk ispkeeisls
241  tvelsgtvvk qgylakqghk rknwkvrrfv lrkdpaflhy
     ydpskeenrp vggfslrgsl
301  vsaledngvp tgvkgnvqgn lfkvitkddt hyyiqasska
     eraewieaik klt
```

A "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" may include a subject having a disease, disorder, or condition that is characterized as a myeloproliferative neoplasm (MPN). A "subject in need of treatment" may include a subject having a disease, disorder, or condition that is characterized as a Philadelphia chromosome (Ph)-negative MPN. A "subject in need of treatment" may include a subject having a disease, disorder, or condition that is characterized as acute myeloid leukemia (AML).

New Chemical Entities

New chemical entities and uses for chemical entities, for example as therapeutic agents, are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., $-(CH_2)_n-$ where n is an integer such as an integer between 1 and 20). An exemplary alkylene group is $-CH_2CH_2-$.

The term "haloalkyl" refers to an alkyl group that is substituted with at least one halogen. For example, $-CH_2F$, $-CHF_2$, $-CF_3$, $-CH_2CF_3$, $-CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term “cycloalkylene” refers to a cycloalkyl group that is unsaturated at one or more ring bonds.

The term “partially unsaturated carbocyclyl” refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term “aryl” is art-recognized and refers to a carbocyclic aromatic group. Representative aryl groups include phenyl, naphthyl, anthracenyl, and the like. The term “aryl” includes polycyclic ring systems having two or more carbocyclic rings in which two or more carbons are common to two adjoining rings (the rings are “fused rings”) wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms “heterocyclyl” and “heterocyclic group” are art-recognized and refer to saturated, partially unsaturated, or aromatic 3- to 10-membered ring structures, alternatively 3-to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation “C3-C7” indicates that the heterocyclic ring contains a total of from 3 to 7 ring atoms, inclusive of any heteroatoms that occupy a ring atom position.

The terms “amine” and “amino” are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms “alkoxy” or “alkoxyl” are art-recognized and refer to an alkyl group, as defined above, having an oxygen radical attached thereto. Representative alkoxy groups include methoxy, ethoxy, tert-butoxy and the like.

An “ether” is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term “carbonyl” as used herein refers to the radical —C(O)—.

The term “oxo” refers to a divalent oxygen atom —O—.

The term “carboxamido” as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term “carboxy” as used herein refers to the radical —COOH or its corresponding salts, e.g. —COONa, etc.

The term “amide” or “amido” or “amidyl” as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term “stereoisomers” when used herein consist of all geometric isomers, enantiomers or diastereomers. These compounds may be designated by the symbols “R” or “S,” or “+” or “−” depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)” in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Modulation of Pleckstrin-2 Activity and Expression

The compounds disclosed herein preferably modulate activity and/or expression of Pleckstrin-2 (Plek2). Modulation may include inhibiting or decreasing Plek2 activity or expression. Modulation also may include activating or increasing Plek2 activity or expression. Plek2 activity or expression may be assessed utilizing methods known in the art and the methods disclosed herein, including the methods disclosed in the Examples provided herein. In some embodiments, the compounds decrease or increase Plek2 activity or expression relative to a control (e.g., by at least about 10%, 20%, 30%, 40%, 50%, 60%, 70%, 80%, 90%, 100%, 200%, 300%, 400%, 500%, 600%, 700%, 800%, 900%, 1000% or more (or within a range bounded by any of these values)). In some embodiments, an $IC_{50}$ value for a compound in regard to modulating activity or expression of Plek2 may be determined and preferably the compound has an $IC_{50}$ value of less than about 10 μM, 5 μM, or 1 μM, 0.5 μM, 0.1 μM, 0.05 μM, 0.01 μM, 0.005 μM, or 0.001 μM (or within a range bounded by any of these values).

Pharmaceutical Compositions and Methods of Administration

The compounds disclosed herein may be administered as pharmaceutical compositions and, therefore, pharmaceutical compositions incorporating the compounds are considered to be embodiments of the subject matter disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that disrupts the SEC or inhibits the biological activity of the SEC may be administered as a single compound or in combination with another compound that disrupts the SEC or inhibits the biological activity of the SEC or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1 -sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds disclosed herein or salts, esters, and/or amides, thereof. Solvate forms may include ethanol solvates, hydrates, and the like.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

When it is desired to administer the compound as a suppository, conventional bases can be used. Illustratively, cocoa butter is a traditional suppository base. The cocoa butter can be modified by addition of waxes to raise its melting point slightly. Water-miscible suppository bases, such as polyethylene glycols of various molecular weights, can also be used in suppository formulations.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Targeting Pleckstrin-2 (Plek2) for Treating Cancer

The present inventors have determined that Pleckstrin-2 (Plek2) can be targeted to treat cell proliferative diseases and disorders. As such, the subject matter disclosed herein relates to compounds targeted to Plek2 and compounds and compositions and methods for treating cell proliferative diseases and disorders that include or utilize the disclosed compounds. The compositions and methods typically include or utilize the disclosed compounds as therapeutic agents which inhibit the biological activity or expression of Pleckstrin-2 (Plek2) and collectively may be referred to as "Plek2 inhibitors." Particularly disclosed are small molecule inhibitors of Plek2 biological activity.

In some embodiments, the disclosed compounds have the following Formula I or a salt, hydrate, or solvate thereof:

I

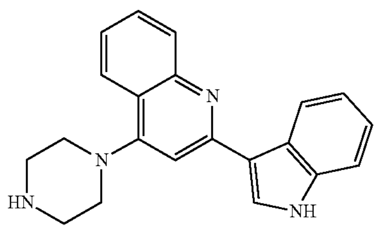

wherein one or more of the carbon atoms of Formula I are substituted with halogen (e.g., C1).

In some embodiments, the disclosed compounds have the following Formula Ia or a salt, hydrate, or solvate thereof:

Ia

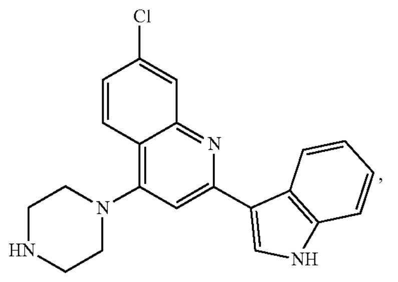

and otherwise may be referred to as "7-chloro-4-(piperazin-1-yl)-2-(1H-indol-3-yl)quinoline," "NUP-52A," or "52A."

In some embodiments of the disclosed compounds, the compounds further may be conjugated to a moiety which targets Plesckin-2 (Plek2) for degradation. For example, the disclosed compounds may be utilized to prepare proteolysis-targeting chimeric molecules (PROTACs) that are targeted to Plek2. PROTACs are heterobifunctional small molecules that simultaneously bind a target protein and a ubiquitin ligase and are known in the art. (See, e.g., Deschaies, "Prime Time for PROTACS," Nature Chem. Biol., 11, 634-635 (2015); Neklesa et al., "Targeted protein degradation by PROTACs," Pharma & Ther., Vol. 174, June 2017, Pages 138-144; Gu et al., "PROTACs: An Emerging Targeting Technique for Protein Degradation in Drug Discovery, " BioEssays, 2018, 40 17000247, 1-11; Bondeson et al., "Lesson in PROTAC Design from Selective Degradation with a Promiscuous Warhead," Cell Chemical Biology, Vol. 25, No. 1, P78-87, (2018); the contents of which are incorporated herein by reference in their entireties). As such, contemplated herein are PROTACs comprising the compounds disclosed herein which simultaneously bind Pleckstrin-2 (Plek2) and ubiquitin ligase.

In some embodiments of the disclosed compounds, the compounds further may be conjugated (e.g., covalently) to an ubiquitin ligase recruiter (e.g., an E3 ligase recruiter), either directly or indirectly via a linker, to form a proteolysis-targeting chimeric molecule (PROTAC) that induces degradation of Plek2. In some embodiments, the molecule has a formula: $M_{Plek2}$-L-$M_{E3}$, wherein $M_{Plek2}$ is a moiety that binds to Plek2 (e.g., such as the compounds disclosed herein), L is a bond or a linker covalently attaching $M_{Plek2}$ and $M_{E3}$, and $M_{E3}$ is a moiety that binds to an E3 ubiquitin ligase.

In some embodiments, the E3 ligase recruiter has a formula:

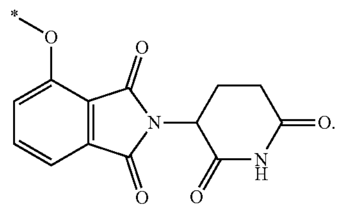 [SMILES: *Oc1cccc2c1C(=O)N(C1CCC(=O)NC1=O)C2=O]

The disclosed compounds may be disclosed directly or indirectly (e.g., via a linker (L)) to an ubiquitin ligase recruiter such as an E3 ligase recruiter. In some embodiments, the compound is conjugated to an E3 ligase recruiter via a linker (L), optionally wherein the linker (L) comprises a moiety having a formula —$(OCH_2CH_2)_n$—NHC(O)— and n is 1-6. In particular, the disclosed compounds may be conjugated indirectly to an E3 ligase recruiter via a linker (L) and may have a formula:

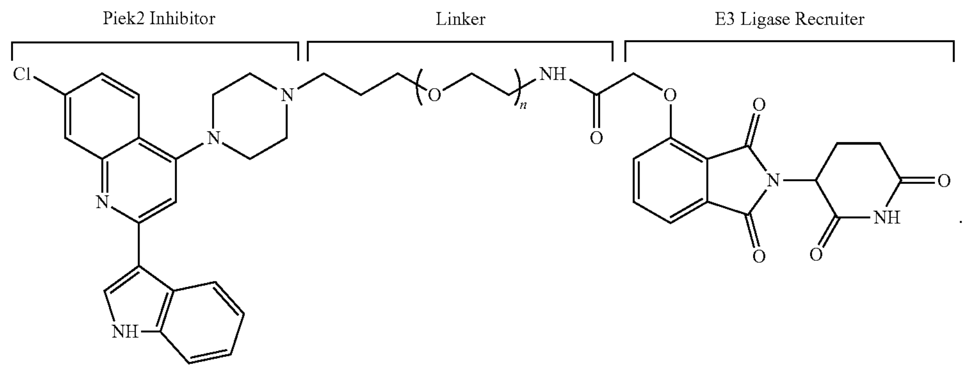

Also disclosed herein are pharmaceutical compositions. For example, disclosed herein are pharmaceutical compositions comprising the compositions disclosed herein optionally together with a suitable pharmaceutical carrier. The pharmaceutical compositions may be administered to a subject in need thereof to treat a disease or disorder as described herein.

In some embodiments, the disclosed pharmaceutical compositions are administered to a subject in need thereof, wherein the subject has a cell proliferative disease or disorder. Suitable cell proliferative diseases and disorders treated by the disclosed methods may include but are not limited to cell proliferative diseases and disorders that are characterized by overexpression of Pleckstrin-2 (Plek2) or activation of the phosphatidylinositide 3-kinase (PI3K)/Akt pathway. Suitable cell proliferative diseases and disorders treated by the disclosed methods may include but are not limited to myeloproliferative neoplasms such as Philadelphia chromosome (Ph)-negative MPNs. Suitable cell proliferative diseases and disorders treated by the methods may include but are not limited to leukemias such as acute myeloid leukemia (AML). In some embodiments, suitable cell proliferative diseases and disorders treated by the disclosed methods may include cancers characterized by a solid tumor.

Illustrative Embodiments

The following Embodiments are illustrative and should not be interpreted to limit the scope of the claimed subject matter.

Embodiment 1. A compound having the following Formula I or a salt, hydrate, or solvate thereof:

I

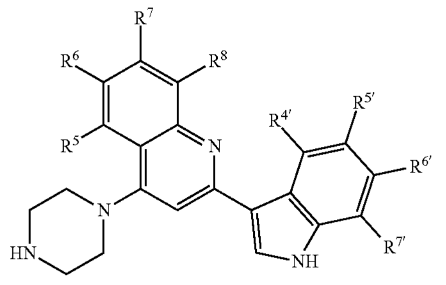

wherein $R^5$, $R^6$, $R^7$, $R^8$, $R^{4'}$, $R^{5'}$, $R^{6'}$, and $R^{7'}$ are hydrogen or halogen.

Embodiment 2. The compound of embodiment 1, wherein at least one of $R^5$, $R^6$, $R^7$, $R^8$, $R^{4'}$, $R^{5'}$, $R^{6'}$, and $R^7$ is halogen.

Embodiment 3. The compound of any of the foregoing embodiments, wherein at least one of $R^5$, $R^6$, $R^7$, $R^8$ is halogen.

Embodiment 4. The compound of any of the foregoing embodiments having a Formula Ia or a salt, hydrate, or solvate thereof:

Ia

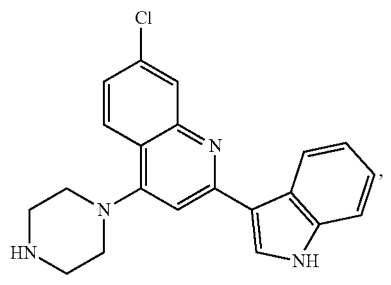

Embodiment 5. The compound of any of the foregoing embodiments which is 7-chloro-4-(piperazin-1-yl)-2-(1H-indol-3-yl)quinoline.

Embodiment 6. The compound of any of the foregoing embodiments further conjugated to an E3 ligase recruiter of a formula:

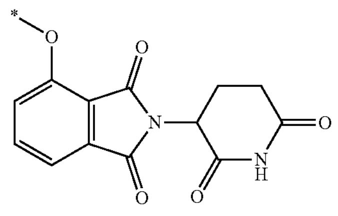 [SMILES: *Oc1cccc2c1C(=O)N(C1CCC(=O)NC1=O)C2=O]

Embodiment 7. The compound of embodiment 6, wherein the compound is conjugated to the E3 ligase recruiter via a linker.

Embodiment 8. The compound of embodiment 7, wherein the linker comprises a moiety having a formula $(-(OCH_2CH_2)_n-NHC(O)-)_n$ and n is 0-6.

Embodiment 9. The compound of embodiment 8 having a formula:

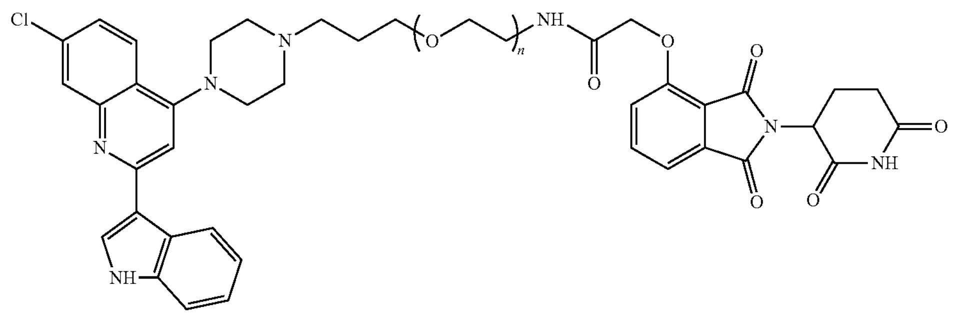

wherein n is 0-6.

Embodiment 10. A pharmaceutical composition comprising the compound of any of the foregoing embodiments and a suitable pharmaceutical carrier.

Embodiment 11. A method for treating a disease or disorder in a subject in need thereof, the method comprising administering to the subject an effective amount of the compound of any of embodiments 1-9 or the pharmaceutical composition of embodiment 10 for inhibiting the activity of Pleckstrin-2 (Plek2).

Embodiment 12. The method of embodiment 11, wherein the disease or disorder is associated with expression and/or activity of Pleckstrin-2 (Plek2).

Embodiment 13. The method of embodiment 11 or 12, wherein the disease or disorder is characterized by overexpression of Pleckstrin-2 (Plek2) or activation of the phosphatidylinositide 3-kinase (PI3K)/Akt pathway.

Embodiment 14. The method of any of embodiments 11-13, wherein the disease or disorder is a cell proliferative disease or disorder.

Embodiment 15. The method of embodiment 14, wherein the cell proliferative disease or disorder is a Philadelphia chromosome (Ph)-negative myeloproliferative neoplasm (MPN), optionally wherein the disease is acute myeloid leukemia (AML) or other hematological diseases.

Embodiment 16. The method of any of embodiments 11-13, wherein the cell proliferative disease or disorder is a cancer characterized by a solid tumor.

Embodiment 17. A compound having a formula: $M_{Plek2}$-L-$M_{E3}$, wherein $M_{Plek2}$ is a moiety that binds to Plek2, L is a bond or a linker covalently attaching $M_{Plek2}$ and $M_{E3}$, and $M_{E3}$ is a moiety that binds to an E3 ubiquitin ligase.

EXAMPLES

The following Examples are illustrative and should not be interpreted to limit the scope of the claimed subject matter.

Example 1—Targeting Pleckstrin-2 (Plek2) for Treating Myeloproliferative Neoplasms (MPNs), Other Cancers, and Other Diseases and Disorders Associated with Plek2 Activity

Abstract

Myeloproliferative neoplasms (MPNs) are a group of bone marrow diseases with excessive production of myeloid cells and increased risk of evolving to acute myeloid leukemia. JAK2V617F mutation is the leading cause of the Philadelphia chromosome (Ph)-negative MPNs (1-5). The discovery of this driver mutation led to the development of JAK inhibitors for the treatment of MPNs. Reduction in spleen size and blood cell counts has been reported in MPN patients treated with JAK inhibitor ruxolitinib (6, 7). However, distinct from the targeted therapy of BCR-ABL positive chronic myeloid leukemia, JAK2 is indispensable for normal hematopoiesis. Significant side effects including anemia and thrombocytopenia were inevitable when high doses of ruxolitinib were attempted (8). In addition, JAK inhibitor is not curative for the disease. Most patients with chronic JAK inhibitor treatment failed to reach molecular and pathologic remissions (6). MPN cells can also acquire adaptive resistance to chronic JAK inhibitor treatment through heterodimerization and transactivation of JAK2 by JAK1 and TYK2 (9). Furthermore, increased incidence of skin tumors or high grade B-cell lymphoma has been revealed in ruxolitinib-treated patients who have prior history of nonmelanoma skin cancers or pre-existing B cell clones, respectively (10, 11). These studies indicate that new targeted therapeutic strategies are needed to treat the disease.

A recently unpublished study identified that Pleckstrin-2 (Plek2), a paralog of Pleckstrin-1 (Plek1) involved in actin dynamics (12-14), was a downstream effector of the JAK2-STATS pathway (15). The authors revealed that Plek2 was overexpressed in JAK2V617F positive MPN patients. Through a mouse genetic approach, the authors further discovered that knockout of Plek2 significantly ameliorated the MPN phenotypes in JAK2V617F knockin mice including reticulocytosis, thrombocytosis, neutrophilia, and splenomegaly. More significantly, loss of Plek2 reverted the widespread vascular occlusions and lethality of JAK2V617F knockin mice (15). These studies demonstrate that Plek2 is critical for the pathogenesis of MPNs with the activated JAK2-STATS pathway, and form a strong foundation for the development of Plek2 inhibitors for the treatment of MPNs. Importantly, this study showed that Plek2 knockout mice did not develop anemia or cytopenia, indicating Plek2's oncogenic potential is only in the disease background and makes Plek2 inhibitor less likely to cause severe side effects.

Here, through medicinal chemistry, novel small molecule Plek2 inhibitors have been identified, which show potent inhibitory effects on several in vitro and in vivo models of MPNs. These compounds are expected to have significant advantages over the current drugs for MPN treatment in that they will decrease the incidence of blood clot formation, which is a major risk of mortality and mobility, and have significant less side effects.

Strategy

Significance. The Philadelphia chromosome (Ph)-negative myeloproliferative neoplasms (MPNs) are a group of bone marrow diseases with excessive production of myeloid cells and increased risk of evolving to acute myeloid leukemia. There are three main types of MPNs: polycythemia vera (PV), essential thrombocythemia (ET), and primary myelofibrosis (PMF). Clinically, PV and ET are characterized by an increased risk of thrombosis, hemorrhage, and evolution to myelofibrosis or acute myeloid leukemia (AML). The major therapeutic goals of PV and ET are to prevent the first occurrence and recurrence of thrombotic complications in the early stages of the diseases (16). Current first-line therapy includes aspirin, hydroxyurea, interferon α, anagrelide, or hydroxycarbamide. However, these treatment approaches remain suboptimal with ongoing risks for thrombosis, hemorrhage, impaired quality of life, and risk of transformation (7, 16). Poor tolerability for interferon α, contradictory leukemogenic risk of hydroxyurea, unresponsive aspirin treatment, and increased risk of arterial thrombosis with anagrelide therapy are all among the major challenges and unmet medical needs in the MPN field.

The JAK2V617F mutation is the leading cause of Ph-negative MPNs (1-5). The discovery of this driver mutation led to the development of JAK inhibitors for the treatment of MPNs (7). Reduction in spleen size and blood cell counts has been reported in MPN patients treated with JAK inhibitor ruxolitinib (6). However, distinct from the targeted therapy of BCR-ABL positive chronic myelogenous leukemia, JAK2 is indispensable for normal hematopoiesis. Significant side effects including anemia and thrombocytopenia were inevitable when high doses of JAK inhibitor were attempted (6, 8). In addition, JAK inhibitor therapy is not curative for the disease. Most patients treated chronically with JAK inhibitors failed to reach molecular and pathologic remissions (8). MPN cells can also acquire adaptive resistance to chronic JAK inhibitor treatment through heterodimerization and transactivation of JAK2 by JAK1 and TYK2 (9). Furthermore, increased incidence of skin tumors or high grade B-cell lymphoma has been revealed in ruxolitinib-treated patients who have prior history of nonmelanoma skin cancers or preexisting B-cell clones, respectively (11, 16). These studies indicate that new targeted therapeutic strategies are urgently needed to treat the disease.

Significantly, patients with Ph-negative MPNs are characterized by a distinct gene expression profile with upregulation of JAK-STAT downstream genes, regardless of the JAK2 mutational status (17). More recent studies further confirmed that patients with calreticulin (CALR) or MPL mutations, the other two major genetic abnormalities in Ph-negative MPNs (18), also involve activation of the JAK-STAT pathway (19, 20). These reports underscore the JAK-STAT pathway in the pathogenesis of MPNs as a valid target for therapy. However, there are currently no therapeutic approaches targeting JAK-STAT effectors.

This provided motivation for research efforts to develop novel compounds targeting the JAK-STAT pathway for the treatment of myeloproliferative neoplasms. In this respect, one recently published study demonstrated a critical role of Plek2, a novel downstream target of JAK2-STATS pathway, in MPN pathogenesis in patients and in a JAK2V617F knock-in mouse model. Using a mouse genetic approach, we demonstrated that loss of Plek2 dramatically ameliorated JAK2V617F-induced reticulocytosis, increased body red cell mass, splenomegaly, and vascular occlusions (15). Importantly, Plek2 knockout mice did not show phenotypic abnormalities including hematologic disorders, indicating Plek2's role in a disease-specific manner (15). These data form the strong foundation for drug development targeting Plek2 for the treatment of MPNs.

To this end, in silico screening of putative Plek2 binding small molecules was performed and the identified hit compounds were shown to exhibit potent in vitro and in vivo effects to block myeloproliferation. This investigation also revealed that Plek2 functions through the phosphoinositide 3-kinase (PI3K) pathway. The identified compounds inhibit Plek2's function through interference of the PI3K pathway and reduction of the phosphorylation of protein kinase B (PKB)/Akt. Therefore, Plek2 functions as a central hub to mediate JAK2-STAT and PI3K-Akt pathways to promote tumor cell proliferation (FIG. 1). Development of Plek2 inhibitors may be useful in disrupting this connection. This study also provides yet another mechanism how PI3K-Akt pathway is activated in MPNs (21-23). The potential therapeutic use of Plek2 inhibitors involves not only the reduction of myeloproliferation through targeting JAK2-STATS effector and PI3K-Akt activation, but also the amelioration of thrombosis through the reduction of whole-body red blood cell mass.

Innovation. If successfully developed as approved pharmaceutical agents, Plek2 inhibitors will represent an important "first-in-class" compound in the field. An important aspect of this innovation relates to the identification of Plek2 as a new target of the JAK2-STATS pathway. Loss of Plek2 significantly ameliorates JAK2V617F-induced myeloproliferation and vascular occlusion.

Approach

Rationale of Targeting Plek2 as a Novel Approach to Treat MPNs.

Figure 2:
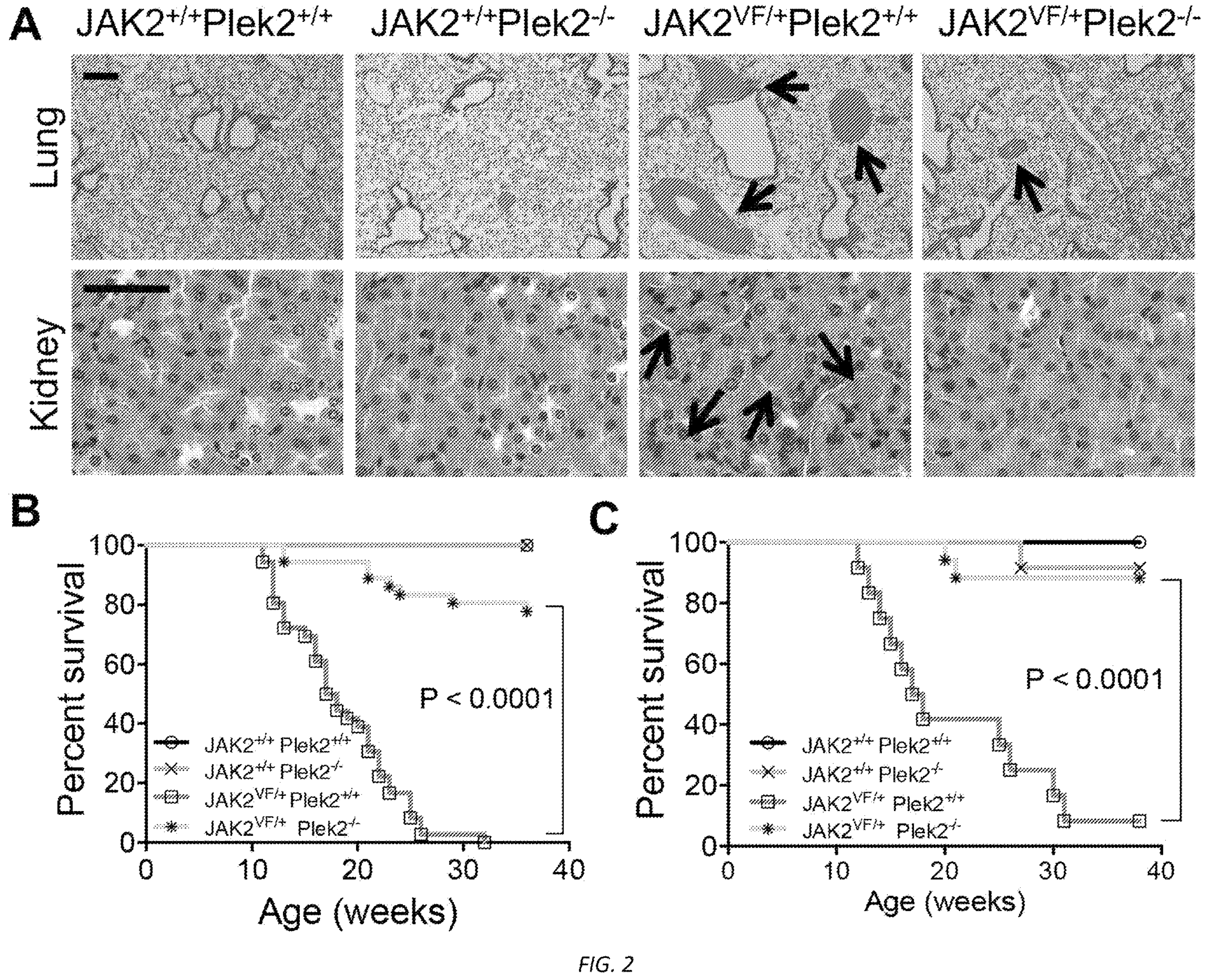
FIG. 2. Loss of Plek2 ameliorates JAK2V617F-induced myeloproliferation and reverts vascular occlusion and lethality. (A) Histologic examination of the lungs and kidneys of the indicated mice. The histologic images are representative of 5 mice in each group analyzed. Arrows indicate vascular occlusions with diameters larger than 50 μm in the lungs (top panels) and numerous small occlusions in the kidneys (bottom panels). Scale bars, 100 μm. (B) Kaplan-Meier survival analysis of indicated mice. Both males and females were included in each group. JAK2+/+ Plek2+/+ mice, n=34; JAK2+/+Plek2−/− mice, n=34; JAK2VF/+Plek2+/+mice, n=36; JAK2VF/+Plek2−/− mice, n=36. (C) Bone marrow mononuclear cells from the indicated mice were transplanted into lethally irradiated wild type mice and monitored for survival as in B. N=10-17 in each group.

A recently published studies identify that Pleckstrin-2 (Plek2), a widely-expressed paralog of Pleckstrin-1 (Plek1) involved in actin dynamics (13, 14), is a downstream effector of the JAK2-STATS pathway (15). Importantly, Plek2 was shown to be overexpressed in JAK2V617F positive MPN patients using real-time PCR, western blotting, and immunohistochemical stain techniques. Through a mouse genetic approach, it was shown that a knockout of Plek2 significantly ameliorated the MPN phenotypes in JAK2V617F knockin mice including reticulocytosis, thrombocytosis, neutrophilia, and splenomegaly. More significant, loss of Plek2 reverted the widespread thrombosis and lethality of JAK2V617F knockin mice (FIG. 2A-B). Transplantation of bone marrow cells from these mice to wild type recipients also revealed the same phenotypes, conforming the hematopoietic-specific roles of Plek2 (FIG. 2C). Significantly, these results revealed that Plek2 knockout mice did not exhibit hematologic abnormalities at a young age. Mild anemia was observed in mice over one year of age, which did not affect the overall survival of Plek2 knockout mice (15). These studies indicate that the pathophysiologic significance of Plek2 was mainly exhibited in the JAK2V617F mutant background, which is important for the development of Plek2 inhibitors to treat MPNs since these agents would be less likely to have severe side effects compared to JAK2 inhibitors. Based on these published work, we have screened for small molecule inhibitors of Plek2 for the treatment of MPNs and thrombosis in these patients.

High throughput screening and hit compound discovery. Plek2 contains two Pleckstrin Homology (PH) domains on the N and C terminus of the protein, which flank a Dishevelled, Eg1-10 and Pleckstrin (DEP) domain in between. Previous loss of function studies on the different domains of Plek2 showed that loss of DEP domain induced the most significant functional defects in Plek2 (14). The crystal structure of Plek2 is currently not available, so we built a homology model of Plek2. Considering the primary amino acid sequence of Plek2 as the query, relevant template structures were identified by homology search using BLAST and PSI-BLAST engines. A comparative homology model of Plek2 was prepared following the method described before (24).

The Plek2 model was then subjected to MolProbity validation and model scored more than 95%, indicating its suitability to carry out further in silico work (25). After validating the model, the Site-Map module from Schrodinger was used to identify the putative ligand binding site along with the druggability score (26). A well-defined binding pocket was identified which also contained the critical residues identified earlier through mutagenesis study (14). A virtual high throughput screening (vHTS) was performed using a 3-tier Glide platform implemented in Schrodinger suite (27). Approximately 100,000 drug-like small molecule compounds were screened that could bind to the Plek2 DEP domain. From this set, compounds that potentially bind to and inhibit the function of Plek2 were identified.

To screen these compounds, an assay using a well-developed Plek2 functional screening system (28) was performed. In this system, mouse fetal liver erythroid progenitors are purified and cultured in erythropoietin containing medium. These cells undergo rapid proliferation closely mimicking accelerated erythropoiesis in MPNs. In these cells, Plek2 is also highly expressed during the culture. This system then may be utilized to test Plek2 inhibitor compounds.

To confirm that the inhibitory effect of compound on the proliferation and differentiation of fetal liver erythroid cells is due to Plek2 binding, Plek2 may be overexpress in the fetal liver cells and treated the cells with Plek2 inhibitors. Indeed, even if a compound is effective, cells with Plek2 overexpression may partially reverted the inhibitory effects of the compound.

In addition, Plek2 may be overexpressed in Cos-7 cells, which may induce prominent lamellipodia formation as previously reported (13). A Plek2 inhibitor then may revert lamellipodia in Plek2 overexpressed cells.

In addition, a binding assay between a Plek2 inhibitor and GST-tagged Plek2 may be performed using isothermal calorimetry (ITC) in order to demonstrate a specific interaction between a Plek2 inhibitor and Plek2.

Rationale and Preliminary Data. Plek2 is a lipid binding protein that has previously been suggested that both PH domains bear the motif to predict specificity for PI3K products (29). The disclosed Plek2 inhibitors may be tested to determine whether the Plek2 inhibitors disrupt Plek2-lipid binding.

The binding of Plek2 to PtdIns(3,4)P2 suggests that Plek2 is a PI3K effector. To further determine the role of Plek2 in PI3K pathway, GFP-fusion Plek2 may be expressed in Jurkat cells and GFP-Plek2 may exhibit membrane as well as cytoplasmic distribution. After treating the cells with the PI3K inhibitor wortmannin, Plek2 cell membrane localization may be significantly disrupted. Bone marrow lineage negative cells from wild type and Plek2 knockout mice may be isolated and treated with erythropoietin to induce their differentiation to erythroid cells. Erythropoietin than may be administered to activate the PI3K pathway leading to the phosphorylation of Akt in the wild type cells. In contrast, phosphorylated Akt may be significantly decreased in Plek2 knockout cells. To directly test a Plek2 inhibitor, the Plek2 inhibitor may be administered to Plek2 wild type bone marrow lineage negative cells treated with erythropoietin, to determine whether the Plek2 inhibitor inhibits phosphorylation of Akt.

Determination of the Extend by which Plek2 Regulations the Cellular Distribution of PtdIns(3,4)$P^2$. Previous studies have shown (31, 32) that hematopoietic cells contain discrete, non-communicating pools of phosphoinositides. Stabilization and modulation of these pools is likely to be very important for phosphoinositide function, and proteins that regulate the distribution of local pools of phosphoinositides are thought to be able to regulate signaling without affecting the overall cellular concentration of these lipids (33, 34). For example, gelsolin binds PtdIns(4,5)P2, and may physically alter its distribution within a membrane bilayer (35). The MARCKS protein is thought to have similar effects (34), and together with GAP43 and CAP23 belongs to a class of proteins called 'PIPmodulins' because they modulate phosphoinositides (36). These proteins are thought to sequester PtdIns(4,5)P2 in the plasma membrane, and they regulate phosphoinositide-mediated signaling (37, 38). In has been hypothesized that Plek2 plays a similar role as a PIPmodulin in that through its reported self-interaction as a homodimer (39), Plek2 promotes phosphoinositide clustering, which could also be facilitated through simple electrostatic effects as described before (34).

To detect the intracellular localization of PtdIns(3,4)P2, retroviruses may be used to express GFP-tagged PH domains of TAPP1 and DAPP1 in the Ter119 negative erythroid progenitor cells treated with erythropoietin. In this case, fetal liver cells from wild type and Plek2 knockout mice may be used for comparison. The PH domains of TAPP1 and DAPP1 have quite different primary sequences, yet both have been well-characterized as specific PtdIns(3,4)P2-binding domains (37, 40). The strength in using these two different fluorescent probes is that the GFP-TAPP1 PH domain and the GFP-DAPP1 PH domain should give identical results if their distribution genuinely reflects the localization of PtdIns(3,4)P2. The same experiment may be performed in erythropoietin-stimulated wild type fetal liver erythroblasts with a Plek2 inhibitor. It might be expected that the distribution of fluorescent PtdIns(3,4)P2 will be altered in Plek2 knockout cells and Plek2 inhibitor treated wild type cells. For comparison, GFP probes that are specific for PtdIns(3,4,5)P3 (such as the PH domains of Grp1) (41) and PtdIns(4,5)P2 (such as the PH domains of *S. cerevisiae* Num1p) (42-44) may be used to determine whether Plek2 affects the localization of other phosphoinositide.

If a Plek2 inhibitor does not affect the lipid binding capacity of Plek2, the Plek2 inhibitor may disrupt Plek2 oligomerization through binding to the DEP domain. To test this, a Plek2 mutant with mutations of amino acids lysine 157, arginine 194, and aspartic acid 166 to alanine may be generated. These three amino acids were known to be critical for Plek2 function and are the predicted binding sites for some Plek2 inhibitors. The mutant may be expressed in Plek2 knockout fetal liver erythroblasts, which is expected to be unable to rescue the altered distribution of PtdIns(3,4)P2 in Plek2 null cells. Wild type Plek2 may be used as the positive control to transduce Plek2 knockout fetal liver erythroblasts.

Determination of the Roles of Plek2 and Plek2 Inhibitors in Akt Phosphorylation in vitro. In vitro cell-free assays may be important to specifically determine the role of Plek2 and Plek2 inhibitors without concerns of off-target effects in vivo in the cells. In vitro assays are available to test Plek2 in clustering phosphoinositides as described in MARCKS and in other PIPmodulins, However, these assays do not directly reveal how Plek2 enhances the PI3K signaling through phosphorylation of Akt. PI3K phosphorylates PtdIns(4,5)P2 to generate PtdIns(3,4,5)P3, which is rapidly dephosphorylated to generate PtdIns(3,4)P2. The 3-phosphate group serves as a docking site on the plasma membrane for the PH domain of Akt, which partially activates Akt. Full activation of Akt requires membrane binding of PH domain containing kinase PDK1 and other kinases including PDK2 or mTORC2 complex to phosphorylate Akt. Using the experiments described herein, the hypothesis that the compounds disrupt Plek2's PtdIns(3,4)P2 clustering ability may be tested. It is also possible that Plek2 interacts with Akt, PDK1, PDK2, or mTORC2 to influence the phosphorylation of Akt. Plek2 inhibitors would therefore block these interactions to inhibit the PI3K-Akt pathway. These two possibilities are not mutually exclusive in that the compounds could play dual roles to inhibit PI3K-Akt pathway through disruption of PtdIns(3,4)P2 clustering and Plek2's interactions with other proteins in the PI3K pathway.

To this end, we GST pull down assays of GST-Plek2 with lysates from Hela cells that express high endogenous levels of Plek2, Akt, and mTOR may be performed. The binding of other proteins in the complex, including HA-Plek2 and mTOR or PDK1 may be tested. The binding assays also may be performed with recombinant Akt, PDK1, PDK2, and mTOR proteins in vitro to demonstrate their direct interaction. The DEP domain may be required for these bindings. To test this, the GST-Plek2 mutant with lysine 157, arginine 194, and aspartic acid 166 mutated to alanine may be utilized, where the mutant might not be expected to exhibit similar binding interactions. With this information, Plek2 inhibitors may be tested to determine the extent they abolish Plek2's interactions with any of these proteins. To ensure that the compounds are specific in blocking the interaction(s), in vitro binding assays using recombinant proteins may be used. To determine that the compounds are specific to Plek2, ITC may be performed to ensure that the compounds do not bind to these proteins. In addition, to determine whether the Plek2 inhibitors can block Plek2-Plek2 self-interaction in an in vitro GST-pull down assay using GST-Plek2 and Flag-tagged Plek2 as previously reported (12, 45) may be performed.

To directly assess the role of Plek2 in clustering phosphoinositide and phosphorylating Akt in vitro an in vitro kinase assay may be performed (46). Recombinant Plek2 may be added (at ~0.1 nM) to vesicles of the desired composition that contain PtdIns(3,4)P2. The ability of this protein-lipid mixture to bind to PDK1, PDK2, or mTORC2, and to stimulate their in vitro kinase activity may be assessed by using Akt as the exogenous substrate. The results of these studies should allow reconciliation of the effects of Plek2 to affect PI3K signaling. This finding may provide insight into the 'capacity' of Plek2 to serve as a phosphoinositide clustering and scaffolding protein for the activation of the PI3K-Akt signaling. Different amount of Plek2 inhibitors may be added in this in vitro kinase assay to determine whether they can inhibit Akt phosphorylation.

Lead Optimization Medicinal Chemistry. The disclosed compound may be used as the starting point in rational and iterative medicinal chemistry optimization. New compounds may be synthesized using suitable synthesis schemes. The new compounds further tested in cell-based and cell-free systems, as well as the binding and kinase assays.

Structure-activity relationships (SAR) may be built by preparing new compounds with modifications at all major positions of the hit structure. Synthesis may take place using parallel chemistry to increase synthetic throughput whenever possible. Each final compound may be purified using reverse-phase preparative HPLC to ensure high (i.e. >95%) purity. Inhibitors may be fully characterized using 1H- and 13C-NMR, HPLC, and MS.

Designed compounds may be docked into a binding model to assess their potential target binding using docked score, binding energy, and overall binding mode (using Schrodiner Glide). In addition, the predicted physiochemical and ADME properties of proposed compounds may be calculated to support the synthesis of compounds expected to possess more pharmaceutical-like characteristics. These parameters may include CLogP, molecular weight, solubility, permeability, and microsomal stability. These may be calculated in both Biovia Pipeline Pilot and ACD/Labs Percepta for increased prediction accuracy and rigor.

Compounds with favorable results in computational experiments may be prioritized for synthesis. Each new final compound may be screened in a cell-based functional assays of proliferation and enucleation. In vitro cell-free binding and kinase assays may be performed to test the efficiency of the newly designed analogs. Inhibitors with $IC_{50}$<10 μM in these assays may be advanced into secondary assays to measure their effects on fetal liver erythroid cells or Cos-7 cells that overexpress Plek2 to confirm Plek2-specificity.

In addition to the design and synthesis of new analogs with improved potency as Plek2 inhibitors, compounds that induce the degradation of Plek2 as another means by which to block the function of Plek2 in MPN may be synthesized. For this, PROTACS (47-50) analogs of the disclosed Plek2 inhibitors may be prepared. While the approach described above focuses on reversible inhibitors of Plek2 function, the PROTACS strategy is complementary in that it leads to complete degradation of the protein and abolishes all of its functions. An example of the type of PROTACS may include a Plek2-binding molecule (e.g. compound NUP-52a) attached through a linker to a molecule that binds to, and recruits, an E3 ligase which will cause ubiquitination of Plek2 and subsequent degradation via the 20S proteasome. For this strategy, a number of different PROTACS derivatives may be synthesized to identify those that cause the most potent and effective Plek2 degradation. These analogs may vary in 1) the point of attachment onto the inhibitor (the SAR generated above may be used to help select the most appropriate derivatization points), 2) the chemistry of the attachment (e.g. alkyl, amide), 3) the type and length of linker (e.g. polyethyleglycol (PEG), alkyl, triazole), 4) the site and chemistry of attachment to the E3 ligand, and 5) the E3-recruiting ligand itself (e.g. VHL ligand, cereblon ligand). New PROTACS compounds may be tested in erythroid or Hela cell western blot to characterize PROTACS-induced degradation. Compounds may be tested at several different concentrations and multiple time points to ensure we accurately define the degradation.

Biophysical Assays and Counter-Screening. To confirm the interaction of the optimized compounds with Plek2, isothermal calorimetry (ITC) may be performed using a recombinant protein GST-Plek2 or Flag-tagged Plek2 as described herein. Specifically, MicroCal ITC200 instrument (GE Healthcare) with the jacket temperature may be set at 25° C. The protein and our compound solutions may be prepared in PBS with 0.5% DMSO. Titrations of 200 μM compound into 20 μM GST-Plek2 solutions will be sufficient for 15 injections of 2.5 μl each with 120 seconds spacing between injections and a mixing speed at 900 rpm. An initial 0.1 μl injection will subsequently be removed during data analysis. A control experiment may be performed by titrating 200 μM compound into a solution of 20 μM GST. Heat signals obtained in this control experiment may be used to correct the ones observed in the compound-GST-Plek2 titration.

Counter screens may be performed to eliminate possible off-target effects of the Plek2 inhibitors disclosed herein. As discussed above, Akt is a direct target of Plek2 in the PI3K pathway. To exclude the possibility that a Plek2 inhibitor directly inhibits Akt phosphorylation, an in vitro kinase assay as described above may be utilized but without the addition of recombinant Plek2. Akt will be phosphorylated by PDK1, PDK2, or mTORC2 in vitro, albeit at a lower level than the assay with the addition of Plek2. In this case, it would be expected that the addition of the compounds will not affect Akt phosphorylation by PDK1, PDK2, or mTORC2.

Additional counter-screenings also may include testing direct binding of the Plek2 inhibitors to other DEP domain containing proteins in order to determine whether the Plek2 inhibitors' bindings are quite specific to Plek2. To this end, biotin-labeled Plek2 inhibitors may be prepared for use in a pull-down assay. The biotinylated compound may be applied to Hela or erythroid cell lysate and streptavidin beads will be added. The biotinylated compound streptavidin-protein complex first may be identified in a Western blot assay for the presence of Plek2. The complex then be applied to a mass spectrometry assay to determine whether additional proteins are present.

Determination of Lead Compound Toxicity. The toxicity of compounds that possess desired bioactivity and in vitro metabolism/absorption as discussed above also may be studied. In these studies, a single dose 'No-Observed-Adverse-Effect-Level (NOAEL)' for compounds may be established in exploratory studies using only wild type mice. A rising dose acute toxicology study may be performed by starting at 25 mg/kg (6 mice per compound, repeated at up to 6 concentrations) and following each animal for 48 hours following a single intraperitoneal (IP) dose for evidence of acute toxicity. The dose may be escalated or decreased until a NOAEL is defined based on clinical observations. Terminal blood samples may be obtained and analyzed for complete blood count and chemistry. The NOAEL may be used to determine the highest dose for PK testing. Toxicity may be determined by standard criteria such as: hunched posture, lack of grooming, failure to thrive, failure to eat and drink, loss of 15-20% body weight, loss of righting reflex. Subsequent studies may use daily dosing for 5 days testing 2-3 dose levels (cohorts of 3-5 mice) selected from the single dose acute toxicity study and considering PK data.

Pharmacokinetic (PK) Assessment. PK studies using the highest safe dose will be conducted on lead compounds that are functionally validated and for which a single dose NOAEL could be established may be performed. IP dosing may be used to obtain data on many PK parameters, including bioavailability, which will be useful in prioritizing and triaging optimized compounds for testing using other routes, e.g., oral. PK parameters may be determined including Cmax, Tmax, VdSS, CIE, AUC, t., and oral bioavailability (% F) may be obtained (with the inclusion of an intravenous dosed cohort). These data may determine if the plasma concentrations are sufficient to provide satisfactory data in animals in the efficacy studies and to determine appropriate doses and dosing schedules for promising compounds. One goal may be to optimize a Plek2 inhibitor to have a plasma AUC>5× its cell viability EC50, a t1/2>2 hrs, and low-to-moderate clearance. Toxicology and pathology measures may be performed after anti-tumor activity of lead compounds has been determined, if compounds are found worthy of detailed study based on MPN efficacy data. This approach may maximize use of animals and resources. In brief, complete blood counts may be obtained; selected organs and tissues (bone marrow, spleen, lung, liver, kidney) may be harvested.

Erythropoietin injection mouse model. The compounds disclosed herein may be tested in MPN mouse models. Selected compounds may first be tested in an erythropoietin (Epo) injection mouse model, which takes significantly less time (3 weeks) to determine the effects of the compounds in vivo. A recently published work using this model demonstrated that repeated injection of Epo induced erythrocytosis, splenomegaly, and vascular occlusions in wild-type mice (15). In contrast, these phenotypes were significantly ameliorated when the same Epo injections were performed in Plek2 knockout mice(15). With the same system, Epo may be injected in wild-type mice at 5,000 U/kg every 2 days for 2 weeks, and test compounds (as Plek2 inhibitors) may be injected one week after Epo injection at 40 mg/kg every 2 days for 8 days. The mice may be sacrificed after 3 weeks to determine their complete blood count, spleen size, and vascular occlusion.

In vivo MPN Mouse Models. The compounds may be tested in MPN mouse models such as the JAK2V617F knock-in model, mouse transplantation models of bone marrow cells transduced with MPL or CALR mutants, and a Ptenfl/flMx-Cre model. Mutations in MPL and CALR represent the other two major causes Ph-negative MPNs. MPL functions physiologically as the thrombopoietin (Tpo) receptor and requires JAK2 to mediate its signaling. MPLW515L is one of the most common mutations and leads to receptor activation independent of Tpo (52). MPL mutations are commonly seen in ET and PMF. A mouse transplantation model using MPLW515L transduced bone marrow cells recapitulates human MPNs including myelofibrosis (53). Mutations in CALR are also commonly seen in patients with ET and PMF. More recent studies reveal that MPL is required for mutant CALR-driven transformation through JAK2-STAT pathway activation. (17, 20). These studies underscore the significance of JAK2-STAT pathway in the pathogenesis of Ph-negative MPNs, which is also confirmed by gene expression profiling data (17, 54). Therefore, it is very likely that Plek2 could also be involved in the pathogenesis of MPL and CALR mutation-driven MPNs.

Compounds may be first tested in experiments described above in the JAK2V617F knockin mouse model based on the PK information obtained in the experiments described above. JAK inhibitor ruxolitinib may be used as a positive control and the control for the measurement of toxicity. DMSO may be used as the negative control. The in vitro $IC_{50,}$ dosages used for test compounds and ruxolitinib, as well as dosages used in the experiments described above may be considered to determine the optimal dosage and dosing schedule of the Plek2 inhibitors to treat JAK2V617F mice. With this information, compounds may be injected retroperitoneally in JAK2V617F MPN mice. The complete blood count every other week and survival may be monitored. The bone marrow and spleen from these mice may be analyzed to determine whether the lead compounds could revert the activated JAK2-STAT5-induced myeloproliferative phenotypes such as hypercellular bone marrow, increased megakaryocytes, granulocytic and erythroid hyperplasia, splenomegaly, and thrombosis (vascular occlusions) at the completion of these injections and when the DMSO control mice start to show phenotype and lethality.

The effect of test compounds in MPLW515L and CALR mutant-induced MPNs also may be assessed. The most studied model with these two mutants is bone marrow transplantation. First the lineage negative, c-Kit positive bone marrow stem/progenitor cells (HSPCs) may be purified from wild type mice. These cells may be transduced with lentiviruses expressing wild-type MPL, MPLW515L mutant, or vector control. The cells ($5\times10^5$, CD45.2+) then may be transplanted into lethally irradiated recipient mice together with wild-type supporting cells ($5\times10^6$, CD45.1+). Similar to JAK2V617F mutation, transplantation of bone marrow cells expressing MPLW515L is known to be able to induce MPN phenotypes in the recipient mice, which include erythrocytosis, leukocytosis, thrombocytosis, and splenomegaly (53). These phenotypes initiate around one month after transplantation and progressively become worse. The mice may be treated one month after transplantation with test compounds using doses and dosing schedule similar to the doses and dosing schedule discussed in JAK2V617F mice above. As a positive control, transplantation of mice with mutant-transduced HSPCs from Plek2 knockout mice also may be performed. Vascular occlusions and lethality in MPLW515L model may be analyzed. In contrast to the JAK2V617F knockin mouse model, mice transplanted with bone marrow cells expressing MPLW515L exhibit prominent myelofibrosis (53). Therefore, whether the test compounds ameliorate fibrosis in the bone marrow and spleen, through reticulin stain, also may be tested.

The CALR mutant contains abundant positively charged amino acid and binds to MPL to induce MPL-dependent myeloproliferative phenotypes (20). Similar to the MPLW515L model, lethally irradiated mice may be transplanted with HSPCs transduced with wild-type human CALR, or a CALRMUT. These mice also may be treated with the test compounds similar to the MPLW515L model. CALRMUT-expressing mice develop megakaryocytic lineage-specific MPN phenotypes including isolated thrombocytosis and megakaryocytic hyperplasia with hyper-lobated nuclei and emperipolesis, which are MPL dependent (13). Because Plek2 is also downstream of the MPL signaling involving JAK2-STAT pathway, and mitigates the megakaryocytic phenotypes in JAK2V617F mice, treatment with Plek2 inhibitors may ameliorate thrombocytosis and megakaryocytic hyperplasia.

Importantly, the MPL and CALR mutant transplantation model may enable determining whether test compounds reduce the allele frequency of the mutant clones after extended period of treatment. In this respect, flow cytometry or PCR may be used to analyze the peripheral white blood cells periodically to determine the percentage of mutant clones (CD45.2+) compared to the normal ones (supporting cells during transplant, CD45.1+). Given this significance, a transplantation model using JAK2V617F will also be performed. Equally important, the long-term treatment with test compounds may reveal whether there is a chronic toxicity to the mice as the JAK inhibitors. In these experiments, JAK inhibitor may be used as the positive control and the control for toxicity analysis.

The Ptenfl/flMx-Cre model may be used to test Plek2 inhibitors. While PTEN is not commonly mutated in patients with MPNs, the activation of the PI3K-Akt pathway is known to be involved in the pathogenesis of MPN (21-23). Because Plek2 is important in the PI3K-Akt pathway, mice with Pten-deficiency-induced MPNs may be treated with test compounds in order to study their mechanism of action in vivo. Ptenfl/flMx-Cre mice may be treated with test compounds ~10-20 days after poly-IC injection with the dosing and dosing schedules similar as above. Then, whether the compounds rescue or delay the lethality of these mice may be determined. One of the advantages of the Ptenfl/flMx-Cre model, compared to the JAK2V617F knockin model and the MPL, CALR mutant transplantation models, is that these mice die of the disease fairly quickly in approximately 40 days. Therefore, dosage may be adjusted to be able to observe the rescue phenotype within a short period. Whether test compounds reduce myeloid cell organ infiltration and myeloproliferation in the bone marrow in these mice also may be assessed.

References

1. Levine R L, Wadleigh M, Cools J, Ebert B L, Wernig G, Huntly B J, Boggon T J, Wlodarska I, Clark J J, Moore S, Adelsperger J, Koo S, Lee J C, Gabriel S, Mercher T, D'Andrea A, Frohling S, Dohner K, Marynen P, Vandenberghe P, Mesa R A, Tefferi A, Griffin J D, Eck M J, Sellers W R, Meyerson M, Golub T R, Lee S J, Gilliland DG. Activating mutation in the tyrosine kinase JAK2 in polycythemia vera, essential thrombocythemia, and myeloid metaplasia with myelofibrosis. Cancer Cell. 2005;7(4):387-97. Epub 2005 Apr. 20. doi: 10.1016/j.ccr.2005.03.023. PubMed PMID: 15837627.
2. Kralovics R, Passamonti F, Buser A S, Teo S S, Tiedt R, Passweg J R, Tichelli A, Cazzola M, Skoda R C. A gain-of-function mutation of JAK2 in myeloproliferative disorders. N Engl J Med. 2005;352(17):1779-90. Epub 2005 Apr. 29. doi: 10.1056/NEJMoa051113. PubMed PMID: 15858187.
3. James C, Ugo V, Le Couedic J P, Staerk J, Delhommeau F, Lacout C, Garcon L, Raslova H, Berger R, Bennaceur-Griscelli A, Villeval J L, Constantinescu S N, Casadevall N, Vainchenker W. A unique clonal JAK2 mutation leading to constitutive signalling causes polycythaemia vera. Nature. 2005;434(7037):1144-8. Epub 2005 Mar. 29. doi: 10.1038/nature03546. PubMed PMID: 15793561.
4. Baxter E J, Scott L M, Campbell P J, East C, Fourouclas N, Swanton S, Vassiliou G S, Bench A J, Boyd E M, Curtin N, Scott M A, Erber W N, Green A R, Cancer Genome P. Acquired mutation of the tyrosine kinase JAK2 in human myeloproliferative disorders. Lancet. 2005;365(9464):1054-61. Epub 2005 Mar. 23. doi: 10.1016/S0140-6736(05)71142-9. PubMed PMID: 15781101.
5. Kralovics R, Teo S S, Buser AS, Brutsche M, Tiedt R, Tichelli A, Passamonti F, Pietra D, Cazzola M, Skoda R C. Altered gene expression in myeloproliferative disorders correlates with activation of signaling by the V617F mutation of Jak2. Blood. 2005;106(10):3374-6. Epub 2005 Aug. 6. doi: 10.1182/blood-2005-05-1889. PubMed PMID: 16081684.
6. Cervantes F, Vannucchi A M, Kiladjian J J, Al-Ali H K, Sirulnik A, Stalbovskaya V, McQuitty M, Hunter D S, Levy R S, Passamonti F, Barbui T, Barosi G, Harrison C N, Knoops L, Gisslinger H, investigators C-I. Three-year efficacy, safety, and survival findings from COMFORT-II, a phase 3 study comparing ruxolitinib with best available therapy for myelofibrosis. Blood. 2013; 122(25):4047-53. Epub 2013 Nov. 1. doi: 10.1182/blood-2013-02-485888. PubMed PMID: 24174625.
7. Sonbol M B, Firwana B, Zarzour A, Morad M, Rana V, Tiu R V. Comprehensive review of JAK inhibitors in myeloproliferative neoplasms. Ther Adv Hematol. 2013;4(1):15-35. Epub 2013 Apr. 24. doi:10.1177/2040620712461047. PubMed PMID: 23610611; PMCID: PMC3629759.
8. Harrison C, Kiladjian J J, Al-Ali H K, Gisslinger H, Waltzman R, Stalbovskaya V, McQuitty M, Hunter D S, Levy R, Knoops L, Cervantes F, Vannucchi A M, Barbui T, Barosi G. JAK inhibition with ruxolitinib versus best available therapy for myelofibrosis. N Engl J Med. 2012;366(9):787-98. Epub 2012 Mar. 2. doi: 10.1056/NEJMoa1110556. PubMed PMID: 22375970.
9. Koppikar P, Bhagwat N, Kilpivaara O, Manshouri T, Adli M, Hricik T, Liu F, Saunders L M, Mullally A, Abdel-Wahab O, Leung L, Weinstein A, Marubayashi S, Goel A, Gonen M, Estrov Z, Ebert B L, Chiosis G, Nimer S D, Bernstein B E, Verstovsek S, Levine R L. Heterodimeric JAK-STAT activation as a mechanism of persistence to JAK2 inhibitor therapy. Nature. 2012; 489(7414):155-9. Epub 2012 Jul. 24. doi: 10.1038/nature11303. PubMed PMID: 22820254; PMCID: PMC3991463.
10. Passamonti F, Maffioli M. The role of JAK2 inhibitors in MPNs 7 years after approval. Blood. 2018;131(22):

2426-35. Epub 2018 Apr. 14. doi: 10.1182/blood-2018-01-791491. PubMed PMID: 29650801.

11. Porpaczy E, Tripolt S, Hoelbl-Kovacic A, Gisslinger B, Bago-Horvath Z, Casanova-Hevia E, Clappier E, Decker T, Fajmann S, Fux DA, Greiner G, Gueltekin S, Heller G, Herkner H, Hoermann G, Kiladjian J J, Kolbe T, Kornauth C, Krauth M T, Kralovics R, Muellauer L, Mueller M, Prchal-Murphy M, Putz E M, Raffoux E, Schiefer A I, Schmetterer K, Schneckenleithner C, Simonitsch-Klupp I, Skrabs C, Sperr W R, Staber P B, Strobl B, Valent P, Jaeger U, Gisslinger H, Sexl V. Aggressive B-cell lymphomas in patients with myelofibrosis receiving JAK1/2 inhibitor therapy. Blood. 2018. Epub 2018 Jun. 17. doi: 10.1182/blood-2017-10-810739. PubMed PMID: 29907599.

12. Abrams C S, Zhang J, Downes C P, Tang X, Zhao W, Rittenhouse S E. Phosphopleckstrin inhibits gbetagamma-activable platelet phosphatidylinositol-4,5-bisphosphate 3-kinase. J Biol Chem. 1996;271(41): 25192-7. Epub 1996 Oct. 11. PubMed PMID: 8810277.

13. Hu M H, Bauman E M, Roll R L, Yeilding N, Abrams C S. Pleckstrin 2, a widely expressed paralog of pleckstrin involved in actin rearrangement. J Biol Chem. 1999;274(31):21515-8. Epub 1999 Jul. 27. PubMed PMID: 10419454.

14. Bach T L, Kerr W T, Wang Y, Bauman E M, Kine P, Whiteman E L, Morgan R S, Williamson E K, Ostap E M, Burkhardt J K, Koretzky G A, Birnbaum M J, Abrams C S. PI3K regulates pleckstrin-2 in T-cell cytoskeletal reorganization. Blood. 2007;109(3):1147-55. Epub 2006 Sep. 30. doi: 10.1182/blood-2006-02-001339. PubMed PMID: 17008542; PMCID: PMC1785144.

15. Zhao B, Mei Y, Cao L, Zhang J, Sumagin R, Yang J, Gao J, Schipma M J, Wang Y, Thorsheim C, Zhao L, Stalker T, Stein B, Wen Q J, Crispino J D, Abrams C S, Ji P. Loss of pleckstrin-2 reverts lethality and vascular occlusions in JAK2V617F-positive myeloproliferative neoplasms. J Clin Invest. 2018;128(1):125-40. Epub 2017 Dec. 5. doi: 10.1172/JCI94518. PubMed PMID: 29202466.

16. Vannucchi A M, Harrison C N. Emerging treatments for classical myeloproliferative neoplasms. Blood. 2017;129(6):693-703. Epub 2016 Dec. 29. doi: 10.1182/blood-2016-10-695965. PubMed PMID: 28028027.

17. Rampal R, Al-Shahrour F, Abdel-Wahab O, Patel J P, Brunel J P, Mermel C H, Bass A J, Pretz J, Ahn J, Hricik T, Kilpivaara O, Wadleigh M, Busque L, Gilliland D G, Golub T R, Ebert B L, Levine R L. Integrated genomic analysis illustrates the central role of JAK-STAT pathway activation in myeloproliferative neoplasm pathogenesis. Blood. 2014;123(22):e123-33. Epub 2014 Apr. 18. doi: 10.1182/blood-2014-02-554634. PubMed PMID: 24740812; PMCID: PMC4041169.

18. Tefferi A, Pardanani A. Myeloproliferative Neoplasms: A Contemporary Review. JAMA Oncol. 2015; 1(1):97-105. Epub 2015 Jul. 17. doi: 10.1001/jamaoncol.2015.89. PubMed PMID: 26182311.

19. Araki M, Yang Y, Masubuchi N, Hironaka Y, Takei H, Morishita S, Mizukami Y, Kan S, Shirane S, Edahiro Y, Sunami Y, Ohsaka A, Komatsu N. Activation of the thrombopoietin receptor by mutant calreticulin in CALRmutant myeloproliferative neoplasms. Blood. 2016;127(10):1307-16. Epub 2016 Jan. 29. doi: 10.1182/blood-2015-09-671172. PubMed PMID: 26817954.

20. Elf S, Abdelfattah N S, Chen E, Perales-Paton J, Rosen E A, Ko A, Peisker F, Florescu N, Giannini S, Wolach O, Morgan E A, Tothova Z, Losman J A, Schneider R K, Al-Shahrour F, Mullally A. Mutant Calreticulin Requires Both Its Mutant C-terminus and the Thrombopoietin Receptor for Oncogenic Transformation. Cancer Discov. 2016;6(4):368-81. Epub 2016 Mar. 10. doi: 10.1158/2159-8290.CD-15-1434. PubMed PMID: 26951227; PMCID: PMC4851866.

21. Bartalucci N, Guglielmelli P, Vannucchi A M. Rationale for targeting the PI3K/Akt/mTOR pathway in myeloproliferative neoplasms. Clin Lymphoma Myeloma Leuk. 2013;13 Suppl 2:S307-9. Epub 2013 Dec. 7. doi: 10.1016/j.clml.2013.07.011. PubMed PMID: 24290217.

22. Choong M L, Pecquet C, Pendharkar V, Diaconu C C, Yong J W, Tai S J, Wang S F, Defour J P, Sangthongpitag K, Villeval J L, Vainchenker W, Constantinescu S N, Lee M A. Combination treatment for myeloproliferative neoplasms using JAK and pan-class I PI3K inhibitors. J Cell Mol Med. 2013;17(11):1397-409. Epub 2013 Nov. 21. doi: 10.1111/jcmm.12156. PubMed PMID: 24251790; PMCID: PMC4117552.

23. Fiskus W, Verstovsek S, Manshouri T, Smith J E, Peth K, Abhyankar S, McGuirk J, Bhalla K N. Dual PI3K/AKT/mTOR inhibitor BEZ235 synergistically enhances the activity of JAK2 inhibitor against cultured and primary human myeloproliferative neoplasm cells. Mol Cancer Ther. 2013;12(5):577-88. Epub 2013 Mar. 1. doi: 10.1158/1535-7163.MCT-12-0862. PubMed PMID: 23445613.

24. Mishra R K, Wei C, Hresko R C, Bajpai R, Heitmeier M, Matulis S M, Nooka A K, Rosen S T, Hruz P W, Schiltz G E, Shanmugam M. In Silico Modeling-based Identification of Glucose Transporter 4 (GLUT4)-selective Inhibitors for Cancer Therapy. J Biol Chem. 2015;290(23):14441-53. Epub 2015 Apr. 8. doi: 10.1074/jbc.M114.628826. PubMed PMID: 25847249; PMCID: PMC4505511.

25. Chen V B, Arendall W B, 3rd, Headd J J, Keedy D A, Immormino R M, Kapral G J, Murray L W, Richardson J S, Richardson D C. MolProbity: all-atom structure validation for macromolecular crystallography. Acta Crystallogr D Biol Crystallogr. 2010;66(Pt 1):12-21. Epub 2010 Jan. 9. doi: 10.1107/S0907444909042073. PubMed PMID: 20057044; PMCID: PMC2803126.

26. Schulz-Gasch T, Stahl M. Binding site characteristics in structure-based virtual screening: evaluation of current docking tools. J Mol Model. 2003;9(1):47-57. Epub 2003 Mar. 15. doi: 10.1007/s00894-002-0112-y. PubMed PMID: 12638011.

27. Sherman W, Day T, Jacobson M P, Friesner R A, Farid R. Novel procedure for modeling ligand/receptor induced fit effects. J Med Chem. 2006;49(2):534-53. Epub 2006 Jan. 20. doi: 10.1021/jm050540c. PubMed PMID: 16420040.

28. Ji P, Jayapal S R, Lodish H F. Enucleation of cultured mouse fetal erythroblasts requires Rac GTPases and mDia2. Nat Cell Biol. 2008;10(3):314-21. Epub 2008 Feb. 12. doi: 10.1038/ncb1693. PubMed PMID: 18264091.

29. Isakoff S J, Cardozo T, Andreev J, Li Z, Ferguson K M, Abagyan R, Lemmon M A, Aronheim A, Skolnik E Y. Identification and analysis of PH domain-containing targets of phosphatidylinositol 3-kinase using a novel in vivo assay in yeast. EMBO J. 1998;17(18):5374-87.

Epub 1998 Sep. 16. doi: 10.1093/emboj/17.18.5374. PubMed PMID: 9736615; PMCID: PMC1170863.
30. Yilmaz O H, Valdez R, Theisen B K, Guo W, Ferguson D O, Wu H, Morrison S J. Pten dependence distinguishes haematopoietic stem cells from leukaemia-initiating cells. Nature. 2006;441(7092):475-82. Epub 2006 Apr. 7. doi: 10.1038/nature04703. PubMed PMID: 16598206.
31. Wang Y, Chen X, Lian L, Tang T, Stalker T J, Sasaki T, Kanaho Y, Brass L F, Choi J K, Hartwig J H, Abrams C S. Loss of PIP5KIbeta demonstrates that PIP5KI isoform-specific PIP2 synthesis is required for IP3 formation. Proc Natl Acad Sci U S A. 2008;105(37): 14064-9. Epub 2008 Sep. 6. doi: 10.1073/pnas.0804139105. PubMed PMID: 18772378; PMCID: PMC2544579.
32. Wang Y, Litvinov R I, Chen X, Bach T L, Lian L, Petrich B G, Monkley S J, Kanaho Y, Critchley D R, Sasaki T, Birnbaum M J, Weisel J W, Hartwig J, Abrams C S. Loss of PIP5KIgamma, unlike other PIP5KI isoforms, impairs the integrity of the membrane cytoskeleton in murine megakaryocytes. J Clin Invest. 2008;118(2):812-9. Epub 2008/01/12. doi: 10.1172/JCI34239. PubMed PMID: 18188447; PMCID: PMC2176194.
33. Caroni P. New EMBO members' review: actin cytoskeleton regulation through modulation of PI(4,5)P(2) rafts. EMBO J. 2001;20(16):4332-6. Epub 2001 Aug. 14. doi: 10.1093/emboj/20.16.4332. PubMed PMID: 11500359; PMCID: PMC125564.
34. McLaughlin S, Murray D. Plasma membrane phosphoinositide organization by protein electrostatics. Nature. 2005;438(7068):605-11. Epub 2005 Dec. 2. doi: 10.1038/nature04398. PubMed PMID: 16319880.
35. Liepina I, Czaplewski C, Janmey P, Liwo A. Molecular dynamics study of a gelsolin-derived peptide binding to a lipid bilayer containing phosphatidylinositol 4,5-bisphosphate. Biopolymers. 2003;71(1):49-70. Epub 2003 Apr. 25. doi: 10.1002/bip.10375. PubMed PMID: 12712500.
36. Laux T, Fukami K, Thelen M, Golub T, Frey D, Caroni P. GAP43, MARCKS, and CAP23 modulate PI(4,5)P (2) at plasmalemmal rafts, and regulate cell cortex actin dynamics through a common mechanism. J Cell Biol. 2000;149(7):1455-72. Epub 2000 Jun. 28. PubMed PMID: 10871285; PMCID: PMC2175130.
37. Lemmon M A. Membrane recognition by phospholipid-binding domains. Nat Rev Mol Cell Biol. 2008; 9(2):99-111. Epub 2008 Jan. 25. doi: 10.1038/nrm2328. PubMed PMID: 18216767.
38. Sheetz M P. Cell control by membrane-cytoskeleton adhesion. Nat Rev Mol Cell Biol. 2001;2(5):392-6. Epub 2001 May 2. doi: 10.1038/35073095. PubMed PMID: 11331914.
39. Hamaguchi N, Ihara S, Ohdaira T, Nagano H, Iwamatsu A, Tachikawa H, Fukui Y. Pleckstrin-2 selectively interacts with phosphatidylinositol 3-kinase lipid products and regulates actin organization and cell spreading. Biochem Biophys Res Commun. 2007;361 (2):270-5. Epub 2007 Jul. 31. doi: 10.1016/j.bbrc.2007.06.132. PubMed PMID: 17658464.
40. Kurokawa T, Takasuga S, Sakata S, Yamaguchi S, Horie S, Homma K J, Sasaki T, Okamura Y. 3' Phosphatase activity toward phosphatidylinositol 3,4-bisphosphate [PI(3,4)P2] by voltage-sensing phosphatase (VSP). Proc Natl Acad Sci U S A. 2012;109 (25):10089-94. Epub 2012 May 31. doi: 10.1073/pnas.1203799109. PubMed PMID: 22645351; PMCID: PMC3382541.
41. Lemmon M A, Ferguson K M, Abrams C S. Pleckstrin homology domains and the cytoskeleton. FEBS Lett. 2002;513(1):71-6. Epub 2002 Mar. 26. PubMed PMID: 11911883.
42. Fischer B, Luthy K, Paesmans J, De Koninck C, Maes I, Swerts J, Kuenen S, Uytterhoeven V, Verstreken P, Versees W. Skywalker-TBC1D24 has a lipid-binding pocket mutated in epilepsy and required for synaptic function. Nat Struct Mol Biol. 2016;23(11):965-73. Epub 2016 Nov. 1. doi: 10.1038/nsmb.3297. PubMed PMID: 27669036.
43. Lemmon M A, Ferguson K M, O'Brien R, Sigler P B, Schlessinger J. Specific and high-affinity binding of inositol phosphates to an isolated pleckstrin homology domain. Proc Natl Acad Sci U S A. 1995;92(23):10472-6. Epub 1995 Nov. 7. PubMed PMID: 7479822; PMCID: PMC40633.
44. Yu J W, Mendrola J M, Audhya A, Singh S, Keleti D, DeWald D B, Murray D, Emr S D, Lemmon M A. Genome-wide analysis of membrane targeting by *S. cerevisiae* pleckstrin homology domains. Mol Cell. 2004;13(5):677-88. Epub 2004 Mar. 17. PubMed PMID: 15023338.
45. Ma A D, Abrams C S. Pleckstrin induces cytoskeletal reorganization via a Rac-dependent pathway. J Biol Chem. 1999;274(40):28730-5. Epub 1999 Sep. 25. PubMed PMID: 10497244.
46. Hresko R C, Murata H, Mueckler M. Phosphoinositide-dependent kinase-2 is a distinct protein kinase enriched in a novel cytoskeletal fraction associated with adipocyte plasma membranes. J Biol Chem. 2003; 278(24):21615-22. Epub 2003 Apr. 19. doi: 10.1074/jbc.M302937200. PubMed PMID: 12682057.
47. Bondeson D P, Smith B E, Burslem G M, Buhimschi A D, Hines J, Jaime-Figueroa S, Wang J, Hamman B D, Ishchenko A, Crews C M. Lessons in PROTAC Design from Selective Degradation with a Promiscuous Warhead. Cell Chem Biol. 2018;25(1):78-87 e5. Epub 2017 Nov. 14. doi: 10.1016/j.chembiol.2017.09.010. PubMed PMID: 29129718; PMCID: PMC5777153.
48. Neklesa T K, Winkler J D, Crews C M. Targeted protein degradation by PROTACs. Pharmacology & therapeutics. 2017;174:138-44. Epub 2017 Feb. 23. doi: 10.1016/j.pharmthera.2017.02.027. PubMed PMID: 28223226.
49. Lonsdale R, Ward RA. Structure-based design of targeted covalent inhibitors. Chemical Society reviews. 2018;47(11):3816-30. Epub 2018 Apr. 6. doi: 10.1039/c7cs00220c. PubMed PMID: 29620097.
50. Butler K V, Ma A, Yu W, Li F, Tempel W, Babault N, Pittella-Silva F, Shao J, Wang J, Luo M, Vedadi M, Brown P J, Arrowsmith C H, Jin J. Structure-Based Design of a Covalent Inhibitor of the SET Domain-Containing Protein 8 (SETD8) Lysine Methyltransferase. J Med Chem. 2016;59(21):9881-9. Epub 2016 Nov. 3. doi: 10.1021/acs.jmedchem.6b01244. PubMed PMID: 27804297; PMCID: PMC5148670.
51. Zhou L P, Yang L H, Tilton S, Wang J L. Development of a high throughput equilibrium solubility assay using miniaturized shake-flask method in early drug discovery. J Pharm Sci-Us. 2007;96(11):3052-71. doi: Doi 10.1002/Jps.20913. PubMed PMID: WOS: 000250618700018.

52. Pikman Y, Lee B H, Mercher T, McDowell E, Ebert B L, Gozo M, Cuker A, Wernig G, Moore S, Galinsky I, DeAngelo D J, Clark J J, Lee S J, Golub T R, Wadleigh M, Gilliland D G, Levine R L. MPLW515L is a novel somatic activating mutation in myelofibrosis with myeloid metaplasia. PLoS Med. 2006;3(7):e270. Epub 2006 Jul. 13. doi: 10.1371/journal.pmed.0030270. PubMed PMID: 16834459; PMCID: PMC1502153.

53. Wen Q J, Yang Q, Goldenson B, Malinge S, Lasho T, Schneider R K, Breyfogle L J, Schultz R, Gilles L, Koppikar P, Abdel-Wahab O, Pardanani A, Stein B, Gurbuxani S, Mullally A, Levine R L, Tefferi A, Crispino J D. Targeting megakaryocytic-induced fibrosis in myeloproliferative neoplasms by AURKA inhibition. Nat Med. 2015;21(12):1473-80. Epub 2015 Nov. 17. doi: 10.1038/nm.3995. PubMed PMID: 26569382; PMCID: PMC4674320.

54. Kleppe M, Kwak M, Koppikar P, Riester M, Keller M, Bastian L, Hricik T, Bhagwat N, McKenney A S, Papalexi E, Abdel-Wahab O, Rampal R, Marubayashi S, Chen J J, Romanet V, Fridman J S, Bromberg J, Teruya-Feldstein J, Murakami M, Radimerski T, Michor F, Fan R, Levine R L. JAK-STAT pathway activation in malignant and nonmalignant cells contributes to MPN pathogenesis and therapeutic response. Cancer Discov. 2015;5(3):316-31. Epub 2015 Jan. 13. doi: 10.1158/2159-8290.CD-14-0736. PubMed PMID: 25572172; PMCID: PMC4355105.

Example 2—Further Testing and Development of Plek2 Inhibitors

The disclosed Plek2 inhibitors may be tested in the $JAK2^{V617F}$ knockin MPN mouse model. The Plek2 inhibitors may be administered at a dosage and dosing schedule of 25 mg/kg, once every two days. Mice may be treated for one month.

Cell proliferation, differentiation, and enucleation assays may be performed utilizing the disclosed compounds.

Isothermal titration calorimetry (ITC) experiments may be performed on the disclosed compounds.

The disclosed compounds may be scaled-up utilizing suitable synthesis schemes.

It may be desirable to prepare crystallized forms of the disclosed compounds.

Example 3—Loss of pleckstrin-2 Reverts Lethality and Vascular Occlusions in JAK2V617F-Positive Myeloproliferative Neoplasms Reference is made to Zhao et al., "Loss of pleckstrin-2 reverts lethality and vascular occlusions in JAK2V617F-positive myeloproliferative neoplasms, J. Clin. Invest., Nov. 20, 2017, the content of which is incorporated herein by reference in its entirety.

Example 4—Optionally Substituted 4-(piperizan-1-yl)-2-(indol-3-yl)quinolines for Targeting Pleckstrin-2 (Plek2)

Myeloproliferative neoplasms (MPNs) are a group of bone marrow diseases with excessive production of blood cells and increased risk of evolving to acute myeloid leukemia. Current therapies on MPNs are not curative but with significant drug resistance and side effects, which necessitate new therapeutic strategies. Our recent published study identified Pleckstrin-2 (Plek2) as a novel target for the treatment of MPNs. Through medicinal chemistry, we have identified novel small molecule Plek2 inhibitors, which show potent inhibitory effects on several in vitro and in vivo models of MPNs. These compounds are expected to have significant advantages over the current drugs for MPN treatment in that they will decrease the incidence of blood clot formation, which is a major risk of mortality and mobility, and have significant less side effects.

Applications

Applications of the disclosed subject matter include, but are not limited to: (i) the use of Plek2 as a novel biomarker for MPNs and other cancers with high Plek2 expression; (ii) new small molecule inhibitors of Plek2 to treat MPNs and solid tumors; (iii) new molecule inhibitors of Plek2 for the treatment of blood diseases with high Plek2 expression; (iv) new small molecule inhibitors of Plek2 as a research tool to study PI3K pathways.

Advantages

Advantages of the disclosed subject matter include, but are not limited to: (i) targeting Plek2 will have potentially significant less side-effect in treating patients with MPNs and other hematologic malignancies; (ii) targeting Plek2 could also be used in patients in the chronic phase of MPNs to reduce red blood cell mass and reduce the risk of thrombosis; and (iv) potential synergistic effect of Plek2 inhibitors with other compounds in treating MPNs and other cancers.

Current drug development efforts in the field of MPN have focused on JAK2 inhibitors. Our studies have identified a completely novel and unexpected biologic role for Pleckstrin-2 in MPNs. Seeking alternative approaches in treating MPNs, other than with JAK inhibitors is significant and innovative to avoid JAK inhibitor drug resistance and side effects. In addition, the mild phenotype of Plek2 knockout mice suggests that targeting the Plek2 signaling pathway for the treatment of MPNs may be better tolerated than the currently available JAK2 inhibitors.

Brief Summary

The novel NUP-52A compound binds to Plek2 and inhibits its function in driving cell proliferation. The compound was derived from the originally disclosed Plek2 inhibitors. It showed potent effects on mouse erythroblast proliferation that is comparable to a commercially available JAK2 inhibitor.

Technical Description

Figure 3:
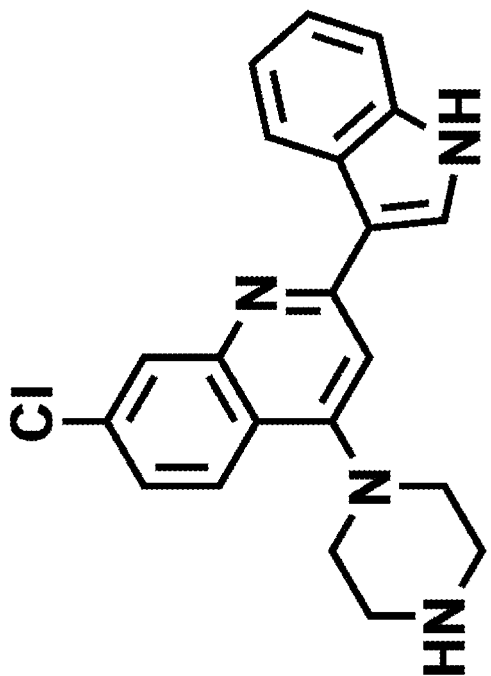
FIG. 3. Structure of NUP-52A.
Figure 4:
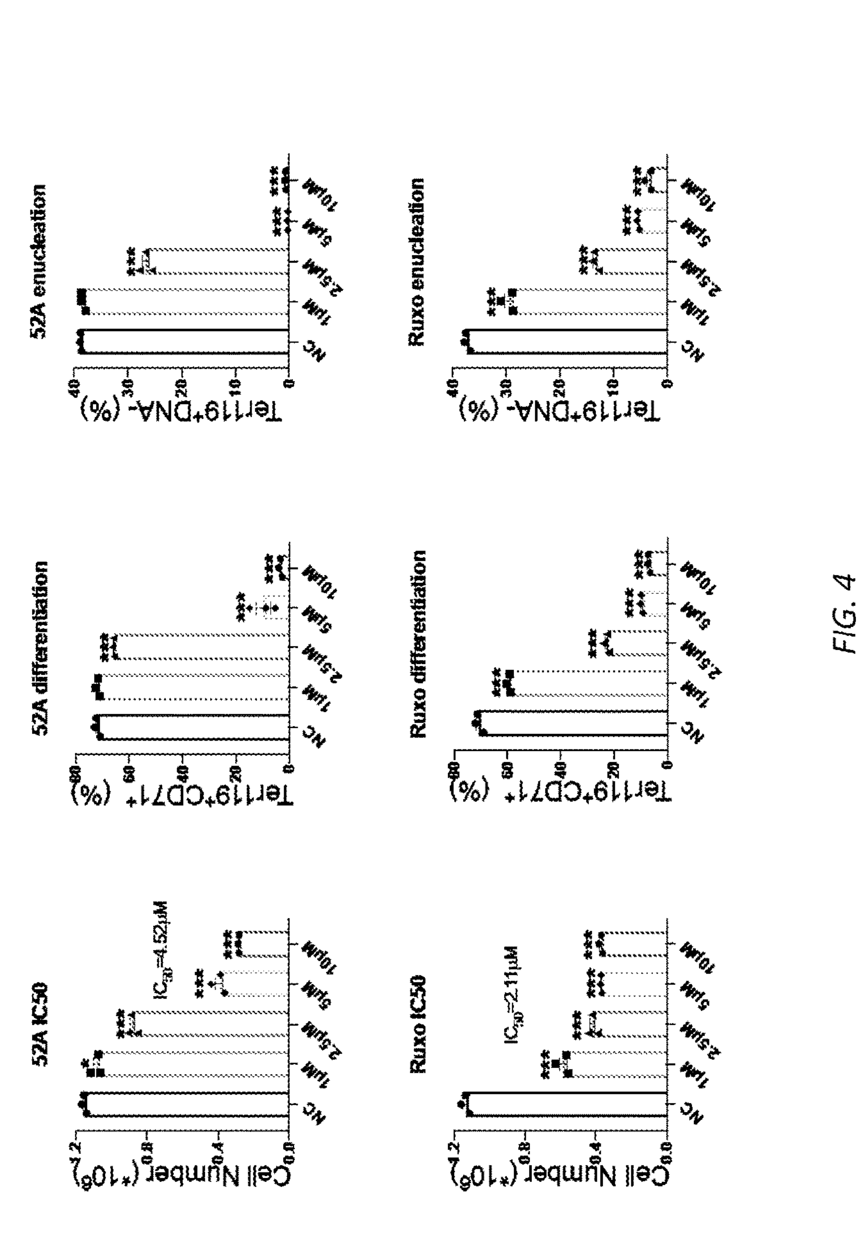
FIG. 4. Effect of NUP-52A on cell proliferation, differentiation, and enucleation in comparison to ruxolitinib. Ter119 negative mouse fetal liver erythroblasts were purified and cultured in erythropoietin containing medium. NUP-52A (Panels A, B, and C) or Ruxolitinib (Panels D, E, and F) with indicated concentrations were added to the culture media at the start of culture. The cells were cultured for two days. Cell proliferation, differentiation, and enucleation were analyzed using flow cytometry on day 2.
Figure 4:
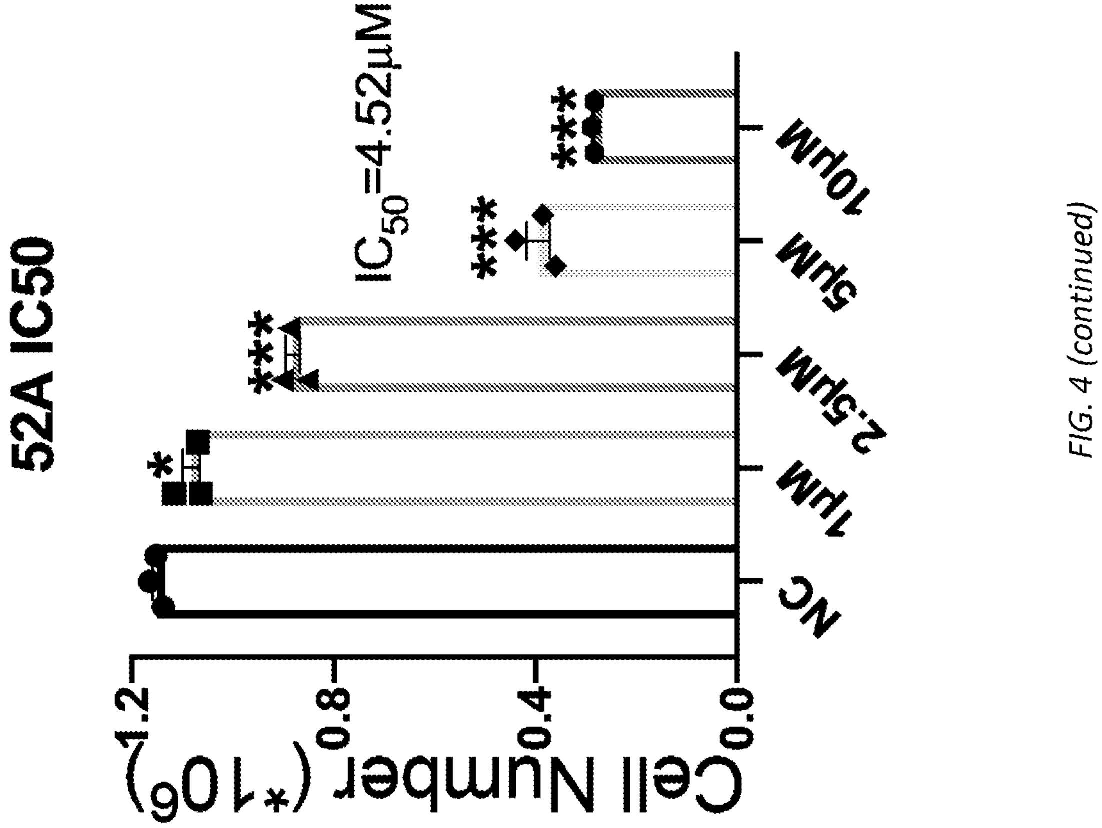
Figure 4:
Figure 4:
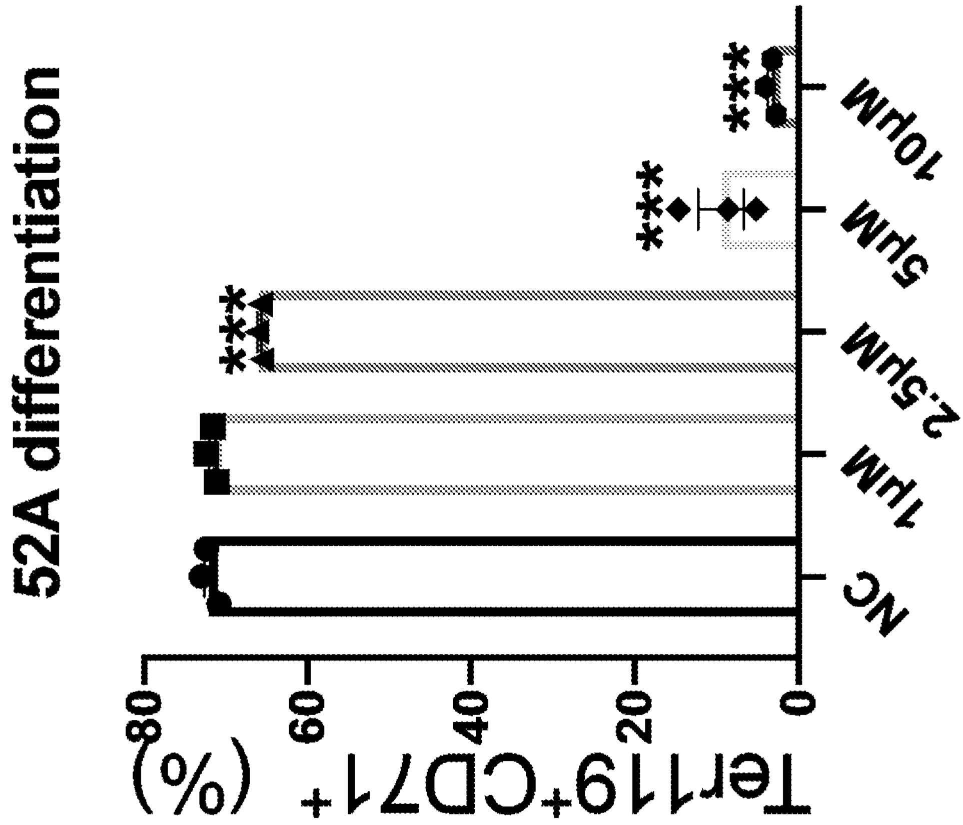
Figure 4:
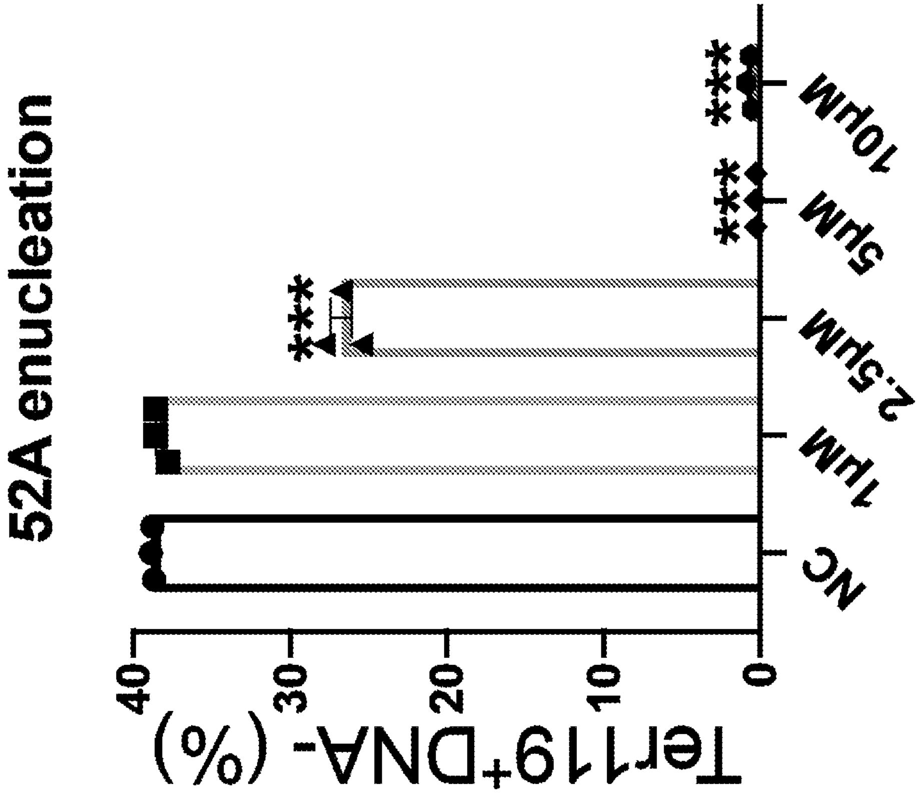
Figure 4:
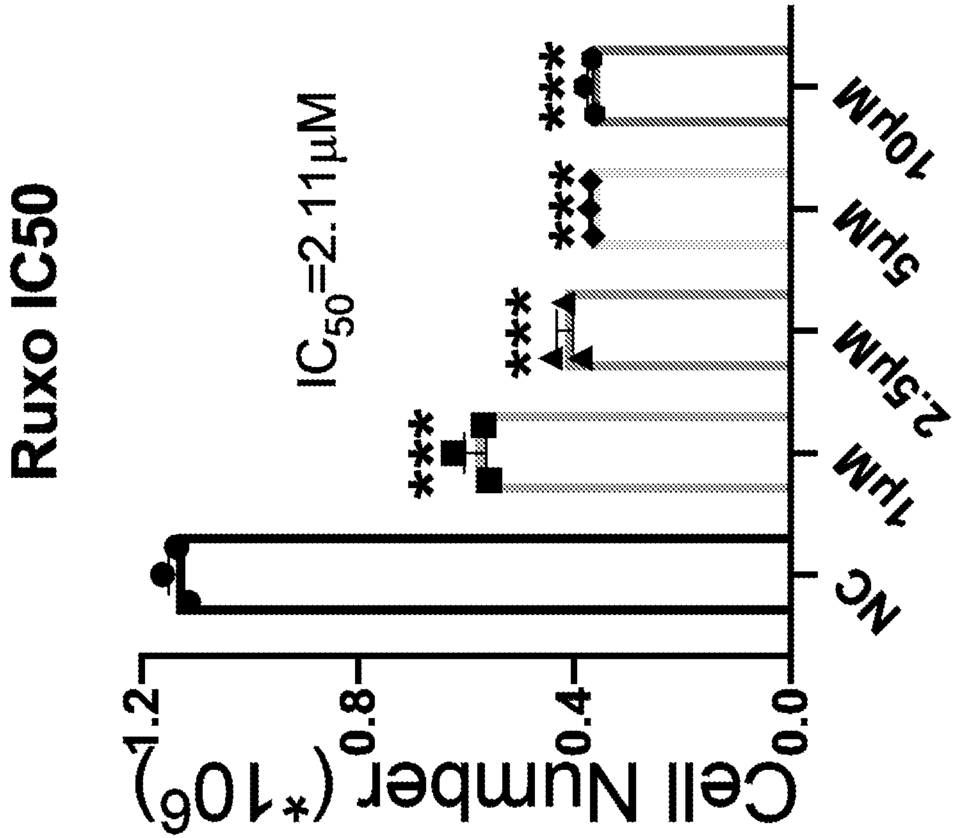
Figure 4:
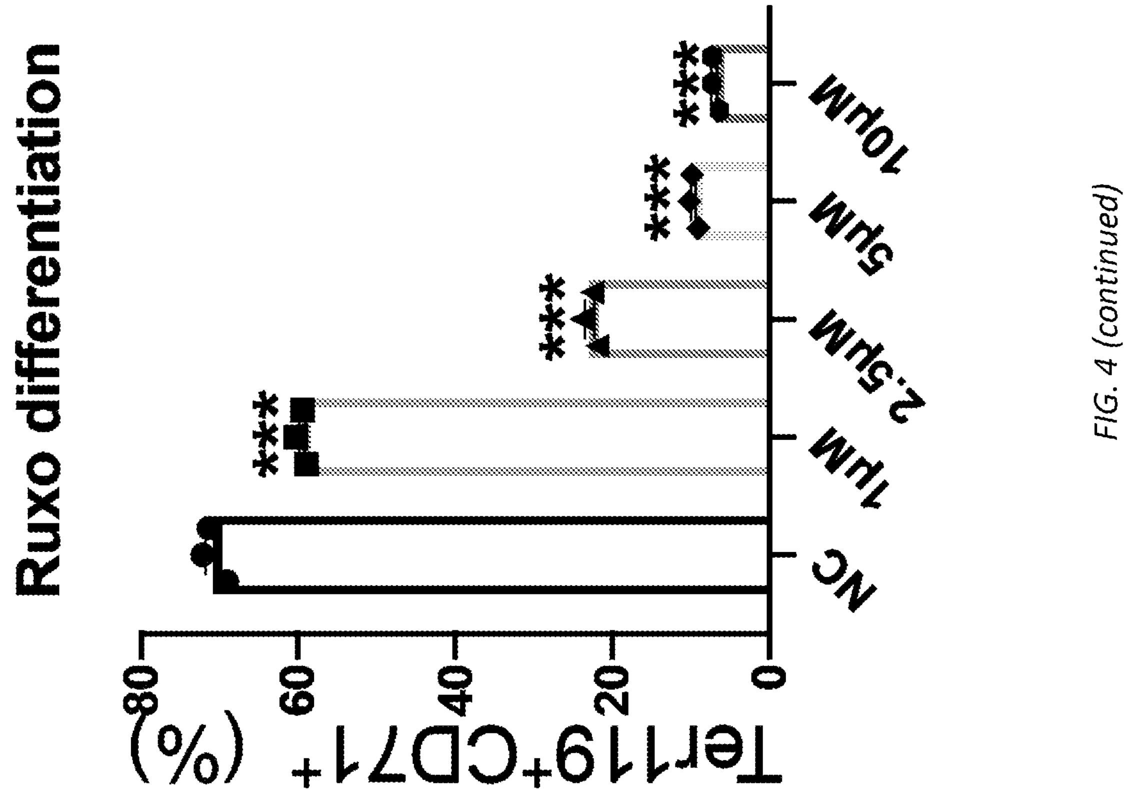
Figure 4:
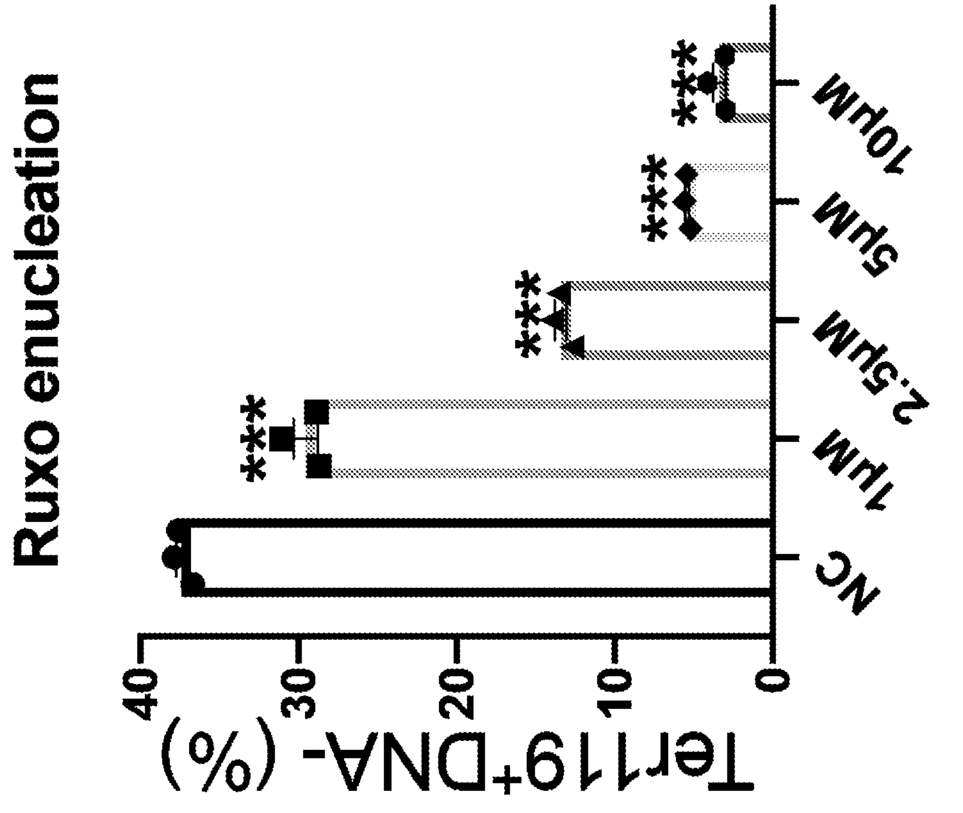

The compound structure is shown in FIG. 3. We used mouse fetal liver erythroblasts to test the compound. Approximately 10 uM NUP-52A was added in the fetal liver erythroblast culture and the proliferation of the cells is monitored daily for two days. Results shown in the data file demonstrate that NUP-52A has strong inhibitory effects on the proliferation of erythroblasts, which is comparable to JAK2 inhibitor Ruxolitinib. (See FIG. 4).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. A compound having the following Formula I or a salt or hydrate thereof:

I

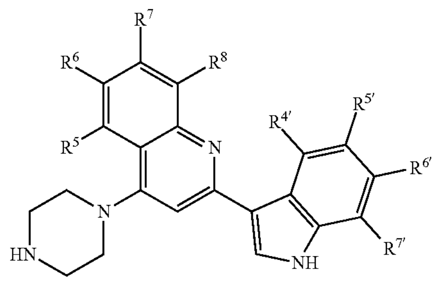

wherein $R^5$, $R^6$, $R^7$, $R^8$, $R^{4'}$, $R^{5'}$, $R^{6'}$, and $R^{7'}$ are hydrogen or halogen.

2. The compound of claim 1, wherein at least one of $R^5$, $R^6$, $R^7$, $R^8$, $R^{4'}$, $R^{5'}$, $R^{6'}$, and $R^{7'}$ is halogen.

3. The compound of claim 1, wherein at least one of $R^5$, $R^6$, $R^7$, $R^8$ is halogen.

4. The compound of claim 1 having a Formula Ia or a salt or hydrate thereof:

Ia

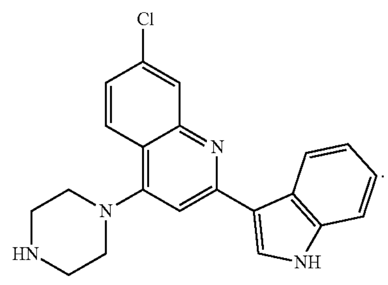

5. The compound of claim 1 which is 7-chloro-4-(piperazin-1-yl)-2-(1H-indol-3-yl)quinoline.

6. A conjugate comprising the compound of claim 1 further conjugated to an E3 ligase recruiter of a formula:

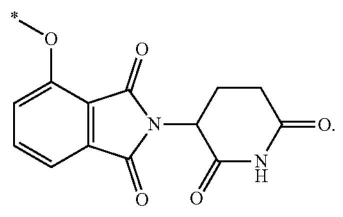 [SMILES: *Oc1cccc2c1C(=O)N(C1CCC(=O)NC1=O)C2=O]

wherein the compound is conjugated to the E3 ligase recruiter via a linker;

wherein the linker comprises a moiety having a formula $(-(OCH_2CH_2)_n-NHC(O)-)_n$ and n is 0-6.

7. The conjugate of claim 6 having a formula:

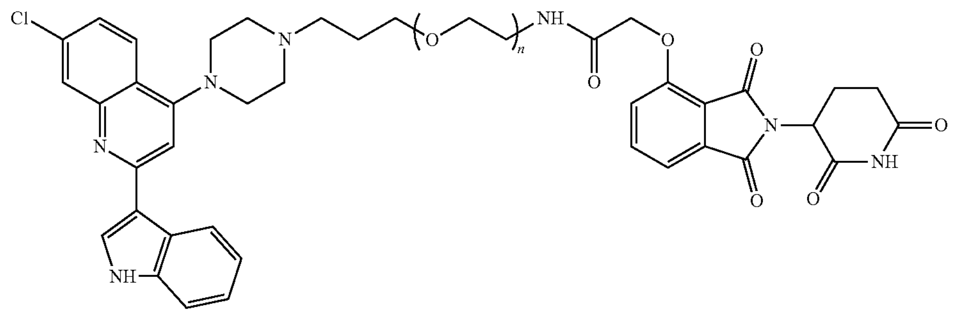

wherein n is 0-6.

8. A pharmaceutical composition comprising the compound of claim 1 and a suitable pharmaceutical carrier.

9. A method for alleviating a disease or disorder in a subject in need thereof, the method comprising administering to the subject an effective amount of the compound of claim 1 for inhibiting the activity of Pleckstrin-2 (Plek2); wherein the disease or disorder is Philadelphia chromosome (Ph)-negative myeloproliferative neoplasm (MPN), acute myeloid leukemia (AML), colorectal carcinoma, pancreatic cancer, lung cancer, renal carcinoma, or breast cancer.

* * * * *

SEQUENCE LISTING

```
<160> NUMBER OF SEQ ID NOS: 1

<210> SEQ ID NO 1
<211> LENGTH: 353
<212> TYPE: PRT
<213> ORGANISM: Homo sapiens

<400> SEQUENCE: 1

Met Glu Asp Gly Val Leu Lys Glu Gly Phe Leu Val Lys Arg Gly His
1               5                   10                  15

Ile Val His Asn Trp Lys Ala Arg Trp Phe Ile Leu Arg Gln Asn Thr
            20                  25                  30

Leu Val Tyr Tyr Lys Leu Glu Gly Gly Arg Arg Val Thr Pro Pro Lys
        35                  40                  45

Gly Arg Ile Leu Leu Asp Gly Cys Thr Ile Thr Cys Pro Cys Leu Glu
    50                  55                  60

Tyr Glu Asn Arg Pro Leu Leu Ile Lys Leu Lys Thr Gln Thr Ser Thr
65                  70                  75                  80

Glu Tyr Phe Leu Glu Ala Cys Ser Arg Glu Glu Arg Asp Ala Trp Ala
                85                  90                  95

Phe Glu Ile Thr Gly Ala Ile His Ala Gly Gln Pro Gly Lys Val Gln
            100                 105                 110

Gln Leu His Ser Leu Arg Asn Ser Phe Lys Leu Pro Pro His Ile Ser
        115                 120                 125

Leu His Arg Ile Val Asp Lys Met His Asp Ser Asn Thr Gly Ile Arg
    130                 135                 140

Ser Ser Pro Asn Met Glu Gln Gly Ser Thr Tyr Lys Lys Thr Phe Leu
145                 150                 155                 160

Gly Ser Ser Leu Val Asp Trp Leu Ile Ser Asn Ser Phe Thr Ala Ser
                165                 170                 175

Arg Leu Glu Ala Val Thr Leu Ala Ser Met Leu Met Glu Glu Asn Phe
            180                 185                 190

Leu Arg Pro Val Gly Val Arg Ser Met Gly Ala Ile Arg Ser Gly Asp
        195                 200                 205

Leu Ala Glu Gln Phe Leu Asp Asp Ser Thr Ala Leu Tyr Thr Phe Ala
    210                 215                 220

Glu Ser Tyr Lys Lys Lys Ile Ser Pro Lys Glu Glu Ile Ser Leu Ser
225                 230                 235                 240

Thr Val Glu Leu Ser Gly Thr Val Val Lys Gln Gly Tyr Leu Ala Lys
                245                 250                 255

Gln Gly His Lys Arg Lys Asn Trp Lys Val Arg Arg Phe Val Leu Arg
            260                 265                 270

Lys Asp Pro Ala Phe Leu His Tyr Tyr Asp Pro Ser Lys Glu Glu Asn
        275                 280                 285
```

-continued

```
Arg Pro Val Gly Gly Phe Ser Leu Arg Gly Ser Leu Val Ser Ala Leu
    290                 295                 300

Glu Asp Asn Gly Val Pro Thr Gly Val Lys Gly Asn Val Gln Gly Asn
305                 310                 315                 320

Leu Phe Lys Val Ile Thr Lys Asp Asp Thr His Tyr Tyr Ile Gln Ala
                325                 330                 335

Ser Ser Lys Ala Glu Arg Ala Glu Trp Ile Glu Ala Ile Lys Lys Leu
            340                 345                 350

Thr
```